(12) United States Patent
van der Burg et al.

(10) Patent No.: US 8,834,519 B2
(45) Date of Patent: *Sep. 16, 2014

(54) METHOD AND DEVICE FOR LEFT ATRIAL APPENDAGE OCCLUSION

(75) Inventors: Erik J. van der Burg, Sunnyvale, CA (US); Dino De Cicco, San Jose, CA (US); Andrew G. C. Frazier, Sunnyvale, CA (US); Alexander K. Khairkhahan, Palo Alto, CA (US); Marc S. Kreidler, Sunnyvale, CA (US); Michael D. Lesh, Mill Valley, CA (US); Chad C. Roue, Fremont, CA (US)

(73) Assignee: Artritech, Inc., Plymouth, MN (US)

( * ) Notice: Subject to any disclaimer, the term of this patent is extended or adjusted under 35 U.S.C. 154(b) by 265 days.

This patent is subject to a terminal disclaimer.

(21) Appl. No.: 13/299,796

(22) Filed: Nov. 18, 2011

(65) Prior Publication Data

US 2012/0065662 A1   Mar. 15, 2012

Related U.S. Application Data

(63) Continuation of application No. 10/674,553, filed on Sep. 30, 2003, now Pat. No. 8,080,032, which is a continuation of application No. 09/435,562, filed on Nov. 8, 1999, now Pat. No. 7,128,073, which is a continuation-in-part of application No. 09/187,200, filed on Nov. 6, 1998, now Pat. No. 6,152,144.

(51) Int. Cl.
| | |
|---|---|
| *A61B 17/08* | (2006.01) |
| *A61M 29/00* | (2006.01) |
| *A61F 2/01* | (2006.01) |
| *A61B 17/12* | (2006.01) |
| *A61M 25/10* | (2013.01) |
| *A61B 17/122* | (2006.01) |
| *A61B 17/00* | (2006.01) |

(52) U.S. Cl.
CPC ........ *A61B 17/12122* (2013.01); *A61B 17/122* (2013.01); *A61B 2017/00867* (2013.01); *A61F 2230/008* (2013.01); *A61B 2017/00557* (2013.01); *A61F 2/01* (2013.01); *A61B 17/0057* (2013.01); *A61B 17/12186* (2013.01); *A61F 2002/018* (2013.01); *A61B 2017/00619* (2013.01); *A61F 2230/0071* (2013.01); *A61M 25/10* (2013.01); *A61B 17/12195* (2013.01); *A61B 2017/00597* (2013.01); *A61F 2230/0006* (2013.01); *A61B 17/12136* (2013.01); *A61F 2230/0069* (2013.01); *A61B 2017/00615* (2013.01); *A61B 2017/00592* (2013.01); *A61B 2017/00601* (2013.01); *A61B 17/12172* (2013.01); *A61M 2025/1054* (2013.01); *A61B 17/12022* (2013.01); *A61B 2017/00575* (2013.01); *A61B 2017/00632* (2013.01); *A61B 2017/1205* (2013.01); *A61B 2017/00579* (2013.01); *A61B 2017/00243* (2013.01); *A61B 2017/081* (2013.01); *A61M 2210/125* (2013.01)
USPC .......................................... 606/213; 606/200

(58) Field of Classification Search
CPC ................. A61B 17/0057; A61B 2017/00575; A61B 2017/00623; A61B 2017/00632
USPC ................... 606/151, 157, 200, 213
See application file for complete search history.

(56) References Cited

U.S. PATENT DOCUMENTS

| | | |
|---|---|---|
| 3,402,710 A | 9/1968 | Paleschuck |
| 3,540,431 A | 11/1970 | Uddin |
| 3,638,652 A | 2/1972 | Kelly |
| 3,844,302 A | 10/1974 | Klein |
| 3,874,388 A | 4/1975 | King et al. |
| 4,007,743 A | 2/1977 | Blake |
| 4,309,776 A | 1/1982 | Berguer |
| 4,341,218 A | 7/1982 | U |
| 4,603,693 A | 8/1986 | Contra et al. |
| 4,611,594 A | 9/1986 | Grayhack et al. |
| 4,638,803 A | 1/1987 | Rand |
| 4,665,906 A | 5/1987 | Jervis |
| 4,681,588 A | 7/1987 | Ketharanathan |
| 4,710,192 A | 12/1987 | Liotta et al. |
| 4,832,055 A | 5/1989 | Palestrant |
| 4,917,089 A | 4/1990 | Sideris |

| Patent | Date | Inventor |
|---|---|---|
| 4,921,484 A | 5/1990 | Hillstead |
| 5,041,090 A | 8/1991 | Scheglov et al. |
| 5,042,707 A | 8/1991 | Taheri |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,234,458 A | 8/1993 | Metais |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,334,217 A | 8/1994 | Das |
| 5,350,398 A | 9/1994 | Pavcnik et al. |
| 5,350,399 A | 9/1994 | Erlebacher et al. |
| 5,375,612 A | 12/1994 | Cottenceau et al. |
| 5,385,148 A | 1/1995 | Lesh et al. |
| 5,397,355 A | 3/1995 | Marin et al. |
| 5,409,458 A | 4/1995 | Khairkhahan et al. |
| 5,417,699 A | 5/1995 | Klein et al. |
| 5,425,744 A | 6/1995 | Fagan et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,464,408 A | 11/1995 | Duc |
| 5,490,856 A | 2/1996 | Person et al. |
| 5,522,790 A | 6/1996 | Moll et al. |
| 5,522,836 A | 6/1996 | Palermo |
| 5,527,322 A | 6/1996 | Klein et al. |
| 5,527,338 A | 6/1996 | Purdy |
| 5,569,204 A | 10/1996 | Cramer |
| 5,614,204 A | 3/1997 | Cochrum |
| 5,634,936 A | 6/1997 | Linden et al. |
| 5,634,942 A | 6/1997 | Chevillon et al. |
| 5,643,282 A | 7/1997 | Kieturakis |
| 5,643,292 A | 7/1997 | Hart |
| 5,669,933 A | 9/1997 | Simon et al. |
| 5,683,411 A | 11/1997 | Kavteladze et al. |
| 5,693,067 A | 12/1997 | Purdy |
| 5,700,285 A | 12/1997 | Myers et al. |
| 5,702,421 A | 12/1997 | Schneidt |
| 5,709,224 A | 1/1998 | Behl et al. |
| 5,709,704 A | 1/1998 | Nott et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,894 A | 5/1998 | Engelson |
| 5,766,219 A | 6/1998 | Horton |
| 5,776,097 A | 7/1998 | Massoud |
| 5,782,860 A | 7/1998 | Epstein et al. |
| 5,785,679 A | 7/1998 | Abolfathi et al. |
| 5,792,064 A | 8/1998 | Panescu et al. |
| 5,800,457 A | 9/1998 | Gelbfish |
| 5,800,512 A | 9/1998 | Lentz et al. |
| 5,830,228 A | 11/1998 | Knapp et al. |
| 5,836,968 A | 11/1998 | Simon et al. |
| 5,843,118 A | 12/1998 | Sepetka et al. |
| 5,849,005 A | 12/1998 | Garrison et al. |
| 5,853,422 A | 12/1998 | Huebsch et al. |
| 5,865,791 A | 2/1999 | Whayne et al. |
| 5,868,680 A | 2/1999 | Steiner et al. |
| 5,879,366 A | 3/1999 | Shaw et al. |
| 5,891,558 A | 4/1999 | Bell et al. |
| 5,904,680 A | 5/1999 | Kordis et al. |
| 5,906,207 A | 5/1999 | Shen |
| 5,911,734 A | 6/1999 | Tsugita et al. |
| 5,921,982 A | 7/1999 | Lesh et al. |
| 5,928,260 A | 7/1999 | Chin et al. |
| 5,935,145 A | 8/1999 | Villar et al. |
| 5,935,148 A | 8/1999 | Villar et al. |
| 5,941,888 A | 8/1999 | Wallace et al. |
| 5,951,599 A | 9/1999 | McCrory |
| 5,961,545 A | 10/1999 | Lentz et al. |
| 5,971,983 A | 10/1999 | Lesh |
| 5,984,929 A | 11/1999 | Bashiri et al. |
| 5,984,937 A | 11/1999 | Morse et al. |
| 5,993,483 A | 11/1999 | Gianotti |
| 6,004,348 A | 12/1999 | Banas et al. |
| 6,007,557 A | 12/1999 | Ambrisco et al. |
| 6,012,457 A | 1/2000 | Lesh |
| 6,013,093 A | 1/2000 | Nott et al. |
| 6,024,740 A | 2/2000 | Lesh et al. |
| 6,024,756 A | 2/2000 | Huebsch et al. |
| 6,059,726 A | 5/2000 | Lee et al. |
| 6,063,070 A | 5/2000 | Eder |
| 6,076,012 A | 6/2000 | Swanson et al. |
| 6,079,414 A | 6/2000 | Roth |
| 6,080,182 A | 6/2000 | Shaw et al. |
| 6,096,053 A | 8/2000 | Bates |
| 6,110,243 A | 8/2000 | Wnenchak et al. |
| 6,117,101 A | 9/2000 | Diederich et al. |
| 6,123,084 A | 9/2000 | Jandak et al. |
| 6,124,523 A | 9/2000 | Banas et al. |
| 6,132,438 A | 10/2000 | Fleischman et al. |
| 6,139,573 A | 10/2000 | Sogard et al. |
| 6,152,144 A | 11/2000 | Lesh et al. |
| 6,156,055 A | 12/2000 | Ravenscroft |
| 6,156,061 A | 12/2000 | Wallace et al. |
| 6,162,214 A | 12/2000 | Mueller et al. |
| 6,164,283 A | 12/2000 | Lesh |
| 6,165,178 A | 12/2000 | Bashiri et al. |
| 6,171,329 B1 | 1/2001 | Shaw et al. |
| 6,176,856 B1 | 1/2001 | Jandak et al. |
| 6,179,809 B1 | 1/2001 | Khairkhahan et al. |
| 6,179,859 B1 | 1/2001 | Bates et al. |
| 6,214,029 B1 | 4/2001 | Thill et al. |
| 6,231,561 B1 | 5/2001 | Frazier et al. |
| 6,231,589 B1 | 5/2001 | Wessman et al. |
| 6,245,064 B1 | 6/2001 | Lesh et al. |
| 6,251,122 B1 | 6/2001 | Tsukernik |
| 6,254,599 B1 | 7/2001 | Lesh et al. |
| 6,258,115 B1 | 7/2001 | Dubrul |
| 6,277,138 B1 | 8/2001 | Levinson et al. |
| 6,290,674 B1 | 9/2001 | Roue et al. |
| 6,305,378 B1 | 10/2001 | Lesh |
| 6,328,727 B1 | 12/2001 | Frazier et al. |
| 6,342,062 B1 | 1/2002 | Suon et al. |
| 6,346,116 B1 | 2/2002 | Brooks et al. |
| 6,350,270 B1 | 2/2002 | Roue |
| 6,352,553 B1 | 3/2002 | van der Burg et al. |
| 6,368,338 B1 | 4/2002 | Konya et al. |
| 6,371,971 B1 | 4/2002 | Tsugita et al. |
| 6,371,972 B1 | 4/2002 | Wallace et al. |
| 6,375,670 B1 | 4/2002 | Greenhalgh |
| 6,383,151 B1 | 5/2002 | Diederich et al. |
| 6,391,044 B1 | 5/2002 | Yadav et al. |
| 6,402,746 B1 | 6/2002 | Whayne et al. |
| 6,402,764 B1 | 6/2002 | Hendricksen et al. |
| 6,402,781 B1 | 6/2002 | Langberg et al. |
| 6,416,511 B1 | 7/2002 | Lesh et al. |
| 6,419,669 B1 | 7/2002 | Frazier et al. |
| 6,425,914 B1 | 7/2002 | Wallace et al. |
| 6,436,088 B2 | 8/2002 | Frazier et al. |
| 6,443,972 B1 | 9/2002 | Bosma et al. |
| 6,447,530 B1 | 9/2002 | Ostrovsky et al. |
| 6,458,100 B2 | 10/2002 | Roue et al. |
| 6,468,266 B1 | 10/2002 | Bashiri et al. |
| 6,468,291 B1 | 10/2002 | Bates et al. |
| 6,471,697 B1 | 10/2002 | Lesh |
| 6,502,576 B1 | 1/2003 | Lesh |
| 6,514,249 B1 | 2/2003 | Maguire et al. |
| 6,514,280 B1 | 2/2003 | Gilson |
| 6,527,769 B2 | 3/2003 | Langberg et al. |
| 6,533,801 B2 | 3/2003 | Wallace et al. |
| 6,537,314 B2 | 3/2003 | Langberg et al. |

| Patent/Publication | Date | Inventor(s) |
|---|---|---|
| 6,547,788 B1 | 4/2003 | Maguire et al. |
| 6,551,302 B1 | 4/2003 | Rosinko et al. |
| 6,551,303 B1 | 4/2003 | Van Tassel et al. |
| 6,561,969 B2 | 5/2003 | Frazier et al. |
| 6,599,308 B2 | 7/2003 | Amplatz |
| 6,615,075 B2 | 9/2003 | Mlynash et al. |
| 6,623,493 B2 | 9/2003 | Wallace et al. |
| 6,641,557 B1 | 11/2003 | Frazier et al. |
| 6,650,923 B1 | 11/2003 | Lesh et al. |
| 6,652,515 B1 | 11/2003 | Maguire et al. |
| 6,652,555 B1 | 11/2003 | Van Tassel et al. |
| 6,652,556 B1 | 11/2003 | Van Tassel et al. |
| 6,689,150 B1 | 2/2004 | VanTassel et al. |
| 6,702,825 B2 | 3/2004 | Frazier et al. |
| 6,706,065 B2 | 3/2004 | Langberg et al. |
| 6,709,456 B2 | 3/2004 | Langberg et al. |
| 6,712,894 B2 | 3/2004 | Shepard |
| 6,716,196 B2 | 4/2004 | Lesh et al. |
| 6,746,472 B2 | 6/2004 | Frazier et al. |
| 6,758,830 B1 | 7/2004 | Schaer et al. |
| 6,810,882 B2 | 11/2004 | Langberg et al. |
| 6,855,144 B2 | 2/2005 | Lesh |
| 6,869,431 B2 | 3/2005 | Maguire et al. |
| 6,872,205 B2 | 3/2005 | Lesh et al. |
| 6,929,633 B2 | 8/2005 | Evans et al. |
| 6,953,460 B2 | 10/2005 | Maguire et al. |
| 6,955,173 B2 | 10/2005 | Lesh |
| 6,955,679 B1 | 10/2005 | Hendricksen et al. |
| 6,964,660 B2 | 11/2005 | Maguire et al. |
| 6,966,908 B2 | 11/2005 | Maguire et al. |
| 6,989,028 B2 | 1/2006 | Lashinski et al. |
| 6,994,092 B2 | 2/2006 | van der Burg et al. |
| 6,997,925 B2 | 2/2006 | Maguire et al. |
| 7,025,756 B2 | 4/2006 | Frazier et al. |
| 7,044,135 B2 | 5/2006 | Lesh |
| 7,056,294 B2 | 6/2006 | Khairkhahan et al. |
| 7,089,063 B2 | 8/2006 | Lesh et al. |
| 7,115,110 B2 | 10/2006 | Frazier et al. |
| 7,128,073 B1 | 10/2006 | van der Burg et al. |
| 7,152,605 B2 | 12/2006 | Khairkhahan et al. |
| 7,175,656 B2 | 2/2007 | Khairkhahan |
| 7,192,439 B2 | 3/2007 | Khairkhahan et al. |
| 7,244,270 B2 | 7/2007 | Lesh |
| 7,340,307 B2 | 3/2008 | Maguire et al. |
| 7,399,271 B2 | 7/2008 | Khairkhahan et al. |
| 7,399,307 B2 | 7/2008 | Evans et al. |
| 7,416,554 B2 | 8/2008 | Lam et al. |
| 7,427,279 B2 | 9/2008 | Frazier et al. |
| 7,510,576 B2 | 3/2009 | Langberg et al. |
| 7,549,983 B2 | 6/2009 | Roue et al. |
| 7,582,051 B2 | 9/2009 | Khairkhahan et al. |
| 7,597,704 B2 | 10/2009 | Frazier et al. |
| 7,674,222 B2 | 3/2010 | Nikolic et al. |
| 7,695,493 B2 | 4/2010 | Saadat et al. |
| 7,713,282 B2 | 5/2010 | Frazier et al. |
| 7,731,681 B2 | 6/2010 | Schaer et al. |
| 7,735,493 B2 | 6/2010 | van der Burg et al. |
| 7,736,378 B2 | 6/2010 | Maahs et al. |
| 7,762,943 B2 | 7/2010 | Khairkhahan |
| 7,763,010 B2 | 7/2010 | Evans et al. |
| 7,780,683 B2 | 8/2010 | Roue et al. |
| 7,780,700 B2 | 8/2010 | Frazier et al. |
| 7,794,444 B2 | 9/2010 | Lesh |
| 7,799,011 B2 | 9/2010 | Lesh |
| 7,862,500 B2 | 1/2011 | Khairkhahan et al. |
| 7,897,086 B2 | 3/2011 | Khairkhahan et al. |
| 7,934,506 B2 | 5/2011 | Woodson et al. |
| 7,935,146 B2 | 5/2011 | Langberg et al. |
| 7,972,359 B2 | 7/2011 | Kreidler |
| 7,976,455 B2 | 7/2011 | Khairkhahan |
| 7,988,726 B2 | 8/2011 | Langberg et al. |
| 7,993,337 B2 | 8/2011 | Lesh |
| 8,038,712 B2 | 10/2011 | Van Der Burg et al. |
| 8,043,305 B2 | 10/2011 | Frazier et al. |
| 8,043,329 B2 | 10/2011 | Khairkhahan et al. |
| 8,080,032 B2 | 12/2011 | van der Burg et al. |
| 8,096,303 B2 | 1/2012 | Dineen et al. |
| 8,142,470 B2 | 3/2012 | Quinn et al. |
| 8,186,355 B2 | 5/2012 | van der Burg et al. |
| 8,192,478 B2 | 6/2012 | Khairkhahan et al. |
| 8,197,496 B2 | 6/2012 | Roue et al. |
| 8,220,466 B2 | 7/2012 | Frazier et al. |
| 8,221,384 B2 | 7/2012 | Frazier et al. |
| 8,241,241 B2 | 8/2012 | Evans et al. |
| 8,246,671 B2 | 8/2012 | Khairkhahan |
| 8,257,428 B2 | 9/2012 | Khairkhahan |
| 8,287,563 B2 | 10/2012 | Khairkhahan |
| 8,296,119 B2 | 10/2012 | Larue, Jr. et al. |
| 8,323,309 B2 | 12/2012 | Khairkhahan et al. |
| 2001/0034537 A1 | 10/2001 | Shaw et al. |
| 2001/0041914 A1 | 11/2001 | Frazier et al. |
| 2002/0022860 A1 | 2/2002 | Borillo et al. |
| 2002/0035374 A1 | 3/2002 | Borillo et al. |
| 2002/0062133 A1 | 5/2002 | Gilson et al. |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2003/0014073 A1 | 1/2003 | Bashiri et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0120337 A1 | 6/2003 | Van Tassel et al. |
| 2003/0135207 A1 | 7/2003 | Langberg et al. |
| 2003/0181942 A1 | 9/2003 | Sutton et al. |
| 2003/0191526 A1 | 10/2003 | Van Tassel et al. |
| 2003/0220667 A1 | 11/2003 | van der Burg et al. |
| 2004/0220610 A1 | 11/2004 | Kreidler et al. |
| 2004/0230222 A1 | 11/2004 | van der Burg et al. |
| 2005/0004652 A1 | 1/2005 | van der Burg et al. |
| 2005/0038470 A1 | 2/2005 | van der Burg et al. |
| 2005/0126563 A1 | 6/2005 | van der Burg et al. |
| 2005/0159727 A1 | 7/2005 | Lesh |
| 2005/0159742 A1 | 7/2005 | Lesh |
| 2005/0165391 A1 | 7/2005 | Maguire et al. |
| 2005/0177182 A1 | 8/2005 | van der Burg et al. |
| 2005/0203568 A1 | 9/2005 | van der Burg et al. |
| 2005/0251131 A1 | 11/2005 | Lesh |
| 2005/0251201 A1 | 11/2005 | Roue et al. |
| 2005/0267498 A1 | 12/2005 | Hendricksen et al. |
| 2006/0009715 A1 | 1/2006 | Khairkhahan et al. |
| 2006/0229491 A1 | 10/2006 | Sharkey et al. |
| 2007/0066993 A1 | 3/2007 | Kreidler |
| 2007/0083227 A1 | 4/2007 | van der Burg et al. |
| 2007/0162048 A1 | 7/2007 | Quinn et al. |
| 2007/0168024 A1 | 7/2007 | Khairkhahan |
| 2007/0213578 A1 | 9/2007 | Khairkhahan et al. |
| 2007/0213815 A1 | 9/2007 | Khairkhahan et al. |
| 2008/0023012 A1 | 1/2008 | Dineen et al. |
| 2008/0027560 A1 | 1/2008 | Jackson et al. |
| 2008/0053461 A1 | 3/2008 | Hirotsuka et al. |
| 2008/0058584 A1 | 3/2008 | Hirotsuka et al. |
| 2008/0086194 A1 | 4/2008 | Kreidler et al. |
| 2008/0228205 A1 | 9/2008 | Sharkey et al. |
| 2008/0319254 A1 | 12/2008 | Nikolic et al. |
| 2009/0018552 A1 | 1/2009 | Lam et al. |
| 2009/0054723 A1 | 2/2009 | Khairkhahan et al. |
| 2009/0171400 A1 | 7/2009 | van der Burg et al. |
| 2009/0204183 A1 | 8/2009 | Kreidler et al. |
| 2009/0254195 A1 | 10/2009 | Khairkhahan et al. |
| 2009/0287040 A1 | 11/2009 | Khairkhahan et al. |
| 2010/0063542 A1 | 3/2010 | Van Der Burg et al. |
| 2010/0121132 A1 | 5/2010 | Nikolic et al. |
| 2010/0121348 A1 | 5/2010 | van der Burg et al. |
| 2010/0234885 A1 | 9/2010 | Frazier et al. |
| 2010/0262168 A1 | 10/2010 | Khairkhahan et al. |
| 2010/0274227 A1 | 10/2010 | Khairkhahan et al. |
| 2010/0324533 A1 | 12/2010 | Lesh |
| 2011/0009957 A1 | 1/2011 | Langberg et al. |
| 2011/0054381 A1 | 3/2011 | Van Dam et al. |
| 2011/0087066 A1 | 4/2011 | Boutillette et al. |
| 2011/0218566 A1 | 9/2011 | van der Burg et al. |
| 2011/0245850 A1 | 10/2011 | van der Burg et al. |
| 2011/0264204 A1 | 10/2011 | Khairkhahan |
| 2011/0270031 A1 | 11/2011 | Frazier et al. |
| 2012/0035643 A1 | 2/2012 | Khairkhahan et al. |
| 2012/0041556 A1 | 2/2012 | van der Burg et al. |
| 2012/0065662 A1 | 3/2012 | van der Burg et al. |

| | | | |
|---|---|---|---|
| 2012/0095539 A1 | 4/2012 | Khairkhahan et al. | |
| 2012/0111341 A1 | 5/2012 | Dineen et al. | |
| 2012/0116489 A1 | 5/2012 | Khairkhahan et al. | |
| 2012/0158111 A1 | 6/2012 | Khairkhahan et al. | |
| 2012/0165827 A1 | 6/2012 | Khairkhahan et al. | |
| 2012/0179157 A1 | 7/2012 | Frazier et al. | |
| 2012/0197373 A1 | 8/2012 | Khairkhahan et al. | |
| 2012/0197388 A1 | 8/2012 | Khairkhahan et al. | |
| 2012/0216818 A1 | 8/2012 | Burg et al. | |
| 2012/0232585 A1 | 9/2012 | Roue et al. | |
| 2012/0239083 A1 | 9/2012 | Kreidler | |
| 2012/0259356 A1 | 10/2012 | Khairkhahan | |
| 2012/0266895 A1 | 10/2012 | Frazier et al. | |
| 2012/0277775 A1 | 11/2012 | Lam et al. | |
| 2012/0283699 A1 | 11/2012 | Evans et al. | |
| 2012/0296340 A1 | 11/2012 | Roue et al. | |

FOREIGN PATENT DOCUMENTS

| | | |
|---|---|---|
| WO | 9640356 A1 | 12/1996 |
| WO | 9827868 A1 | 7/1998 |
| WO | 9923976 A1 | 5/1999 |
| WO | 9944510 A1 | 10/1999 |
| WO | 0016705 A1 | 3/2000 |
| WO | 0067669 A1 | 11/2000 |
| WO | 0115629 A1 | 3/2001 |
| WO | 0130266 A1 | 5/2001 |
| WO | 0130267 A1 | 5/2001 |
| WO | 0130268 A1 | 5/2001 |

*Primary Examiner* — Darwin Erezo

*Assistant Examiner* — Jonathan Hollm

(74) *Attorney, Agent, or Firm* — Seager, Tufte & Wickhem LLC

(57) ABSTRACT

A device and method for obliterating or occluding a body cavity or passageway, in particular, the left atrial appendage of a patient's heart. The procedure can be carried out intra-operatively, but is preferably carried out percutaneously by use of a delivery catheter to position an occluding device adjacent a patient's left atrial appendage. The occluding device may prevent the passage of embolic or other material to or from the left atrial appendage by volumetrically filling the appendage, closing the opening of the appendage with an occluding member, or pulling the tissue around the opening of the appendage together and fixing it in a closed state.

16 Claims, 13 Drawing Sheets

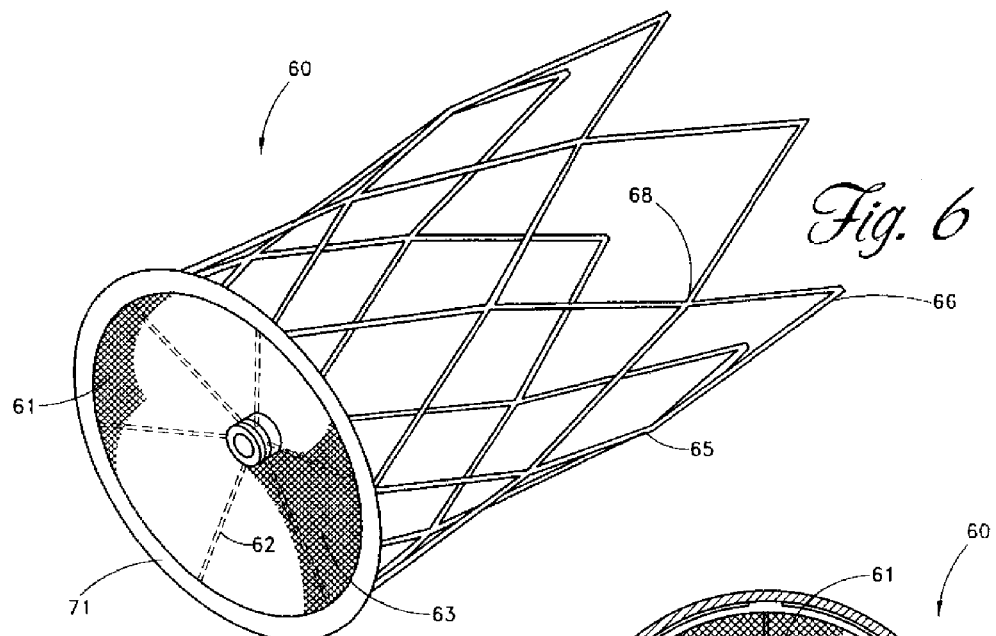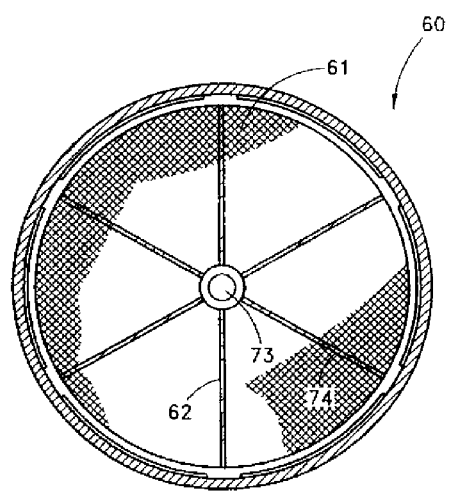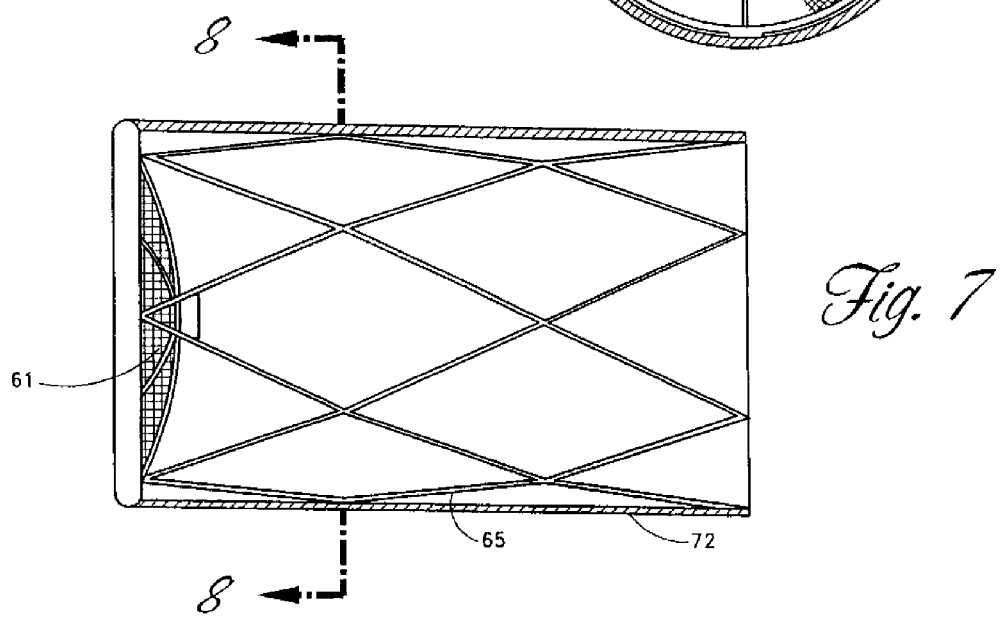

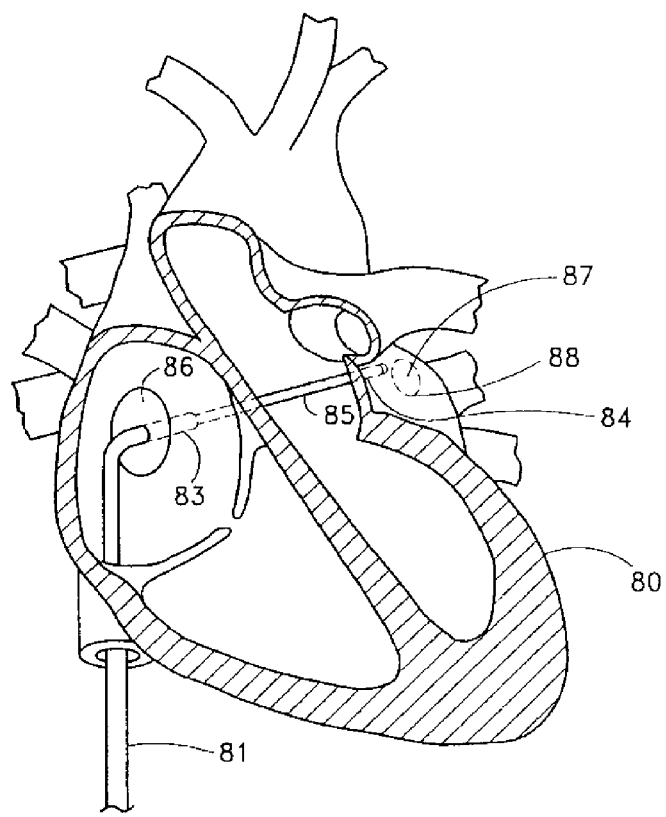
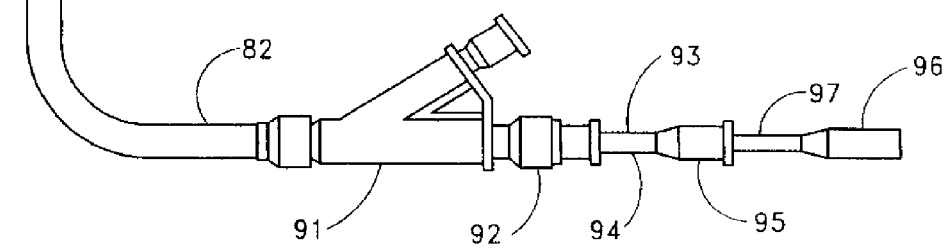
Fig. 9

METHOD AND DEVICE FOR LEFT ATRIAL APPENDAGE OCCLUSION

CROSS-REFERENCE TO RELATED APPLICATIONS

This application is a continuation of application Ser. No. 10/674,553, filed Sep. 30, 2003, which is a continuation of application Ser. No. 09/435,562, filed Nov. 8, 1999, now U.S. Pat. No. 7,128,073, which is a continuation-in-part of application Ser. No. 09/187,200, filed Nov. 6, 1998, now U.S. Pat. No. 6,152,144. The entirety of U.S. Pat. No. 6,152,144 is hereby incorporated by reference.

BACKGROUND

Embolic stroke is the nation's third leading killer for adults, and is a major cause of disability. There are over 80,000 strokes per year in the United States alone. The most common cause of embolic stroke emanating from the heart is thrombus formation due to atrial fibrillation. Atrial fibrillation is an arrhythmia of the heart that results in a rapid and chaotic heartbeat that produces lower cardiac output and irregular and turbulent blood flow in the vascular system. There are over five million people worldwide with atrial fibrillation, with about four hundred thousand new cases reported each year. Atrial fibrillation is associated with a 500 percent greater risk of stroke due to the condition. A patient with atrial fibrillation typically has a significantly decreased quality of life due, in large part, to the fear of a stroke, and the pharmaceutical regimen necessary to reduce that risk.

For patients who have atrial fibrillation and develop atrial thrombus therefrom, the clot normally occurs in the left atrial appendage (LAA) of the heart. The LAA is a cavity which looks like a small finger or windsock and which is connected to the lateral wall of the left atrium between the mitral valve and the root of the left pulmonary vein. The LAA normally contracts with the rest of the left atrium during a normal heart cycle, thus keeping blood from becoming stagnant therein, but often fails to contract with any vigor in patients experiencing atrial fibrillation due to the discoordinate electrical signals associated with AF. As a result, thrombus formation is predisposed to form in the stagnant blood within the LAA. Blackshear and Odell have reported that of the 1288 patients with non-rheumatic atrial fibrillation involved in their study, 221 (17%) had thrombus detected in the left atrium of the heart. Blackshear J L, Odell J A. Appendage obliteration to reduce stroke in cardiac surgical patients with atrial fibrillation. Ann Thorac. Surg., 1996.61(2):755-9. Of the patients with atrial thrombus, 201 (91%) had the atrial thrombus located within the left atrial appendage. The foregoing suggests that the elimination or containment of thrombus formed within the LAA of patients with atrial fibrillation would significantly reduce the incidence of stroke in those patients.

Pharmacological therapies for stroke prevention such as oral or systemic administration of warfarin or the like have been inadequate due to serious side effects of the medications and lack of patient compliance in taking the medication. Invasive surgical or thorascopic techniques have been used to obliterate the LAA, however, many patients are not suitable candidates for such surgical procedures due to a compromised condition or having previously undergone cardiac surgery. In addition, the perceived risks of even a thoroscopic surgical procedure often outweigh the potential benefits. See Blackshear and Odell above. See also Lindsay B D. Obliteration of the left atrial appendage: A concept worth testing. Ann Thorac. Surg., 1996.61(2):515. What has been needed is a less invasive system and method for containment or elimination of thrombus formation in the LAA of patients with atrial fibrillation. The present invention satisfies these and other needs.

SUMMARY

The present invention is directed to a device and method for obliterating or occluding a body cavity or passageway. Specifically, the invention is directed to a device and method for obliterating or occluding the left atrial appendage of a patient's heart, preferably by percutaneous methods which obviate the need for invasive surgical procedures. One purpose of obliterating or occluding a body cavity or passageway, or particularly the left atrial appendage of a patient, is to prevent the passage or egress of embolic material into the bloodstream of a patient.

One embodiment of an apparatus having features of the invention has an occluding member having an outer rim or periphery disposed around the perimeter of the occluding member, with the outer rim configured to sealingly engage a surface of a body cavity. The apparatus also has an anchoring device or means which is secured to the occluding member. The anchoring device or means may include an adhesive between the outer periphery and an inside surface of a body cavity, a suture or sutures which are engaging the outer periphery of the occluding member and the inside surface of the body cavity, or the like. The anchoring device or means serve to secure the outer periphery to a surface of a body cavity or passageway so as to prevent the passage of embolic material or other materials therethrough.

In another embodiment, an apparatus having features of the invention may have an occluding member and a retention member secured to the occluding member. The retention member is configured to engage and attach to a surface of a body cavity and maintain a position of the occluding member to sealingly engage the inside surface of the body cavity and prevent the passage of embolic material or the like therethrough. In embodiments of the apparatus which are intended to occlude a patient's LAA, the occluding member will typically be a frame structure of a high strength material such as stainless steel, a shape memory or pseudoelastic alloy, such as NiTi alloy, or a suitable composite material. The frame structure has a barrier or mesh material disposed over it and preferably secured to it to act as a barrier to the passage of embolic material or fluids. The frame structure serves to support the barrier or mesh material in an outwardly expanded state to substantially occupy at least a portion of the cross section of a body cavity or passageway within which it is disposed. The mesh or barrier material can be any suitable material for preventing the passage of fluids, embolic material or other material suspended in fluids. Typical examples of suitable materials for the barrier include a Nylon or Dacron mesh. Preferably, the barrier or mesh material is made from PTFE or ePTFE having a pore size of up to about 0.04 inches, preferably up to about 0.005 inches. Other suitable materials may include polyurethanes, polyamides, polyethylenes or the like. The outer rim or periphery of the occluding member is preferably made of a soft polymer material which facilitates a seal between the outer rim and the inside surface of the body cavity. The outer rim may have a radial hoop of a metal or other high strength material or composite to provide outward radial pressure on the inside surface of the body cavity, and to maintain the shape of the outer rim. The occluding member may have a transverse dimension of about 0.5 to about 5 cm, preferably about 1 to about 2 cm.

The retention member secured to the occluding member may have any suitable configuration which maintains the position of the occluding member within the body cavity or passageway so as to form at least a substantial seal with the surface therein and prevent the passage of embolic material. Preferably, the retention member is an expandable member configured to engage the inside surface of the body cavity or passageway. The expandable member may be an expandable cylindrically shaped wire structure, typically with linked metallic elements which are capable of self expansion from a constrained state. The expansion member is preferably made from a shape memory or pseudoelastic alloy such as NiTi, or the like, but may also be made from high strength materials such as stainless steel, MP35N and other suitable materials. The expandable member can be covered with a polymer fabric or mesh to act as a buffer between the metallic elements of the expandable member and the inside surface of the body cavity within which it is disposed. The outer sheath may be made of Dacron, Nylon, TFE, PTFE, ePTFE, polyurethane or the like.

In another embodiment of a device having features of the invention, the retention member may be a tissue penetrating shaft which is designed to penetrate an inner wall of a body cavity, preferably the fundus of a body cavity, and be mechanically secured thereto. In a particular embodiment of the tissue penetrating shaft, the distal extremity of the shaft has a helically shaped extension which screws into the tissue of the wall of a body cavity and is thereby mechanically secured thereto. The tissue penetrating shaft may have a length of about 0.5 to about 7 cm, preferably about 1 to about 4 cm, and more preferably about 1.5 to about 3 cm. An alternative embodiment of the tissue penetrating shaft would include radially extending members from the distal end of a shaft in place of or in conjunction with the helically shaped extension. The radially extending members serve to center the shaft within the body cavity or passageway, and also to engage the tissue of the body cavity or passageway to prevent axial movement of the shaft and occluding member. The shaft can have up to about 20 radially extending members, but preferably has about 3 to about 10 radially extending members.

Preferably a method of closing off or blocking a body cavity, in particular a patient's LAA, is performed in a non-invasive or percutaneous manner. Delivery of an occluding device is typically carried out via a Mullin's trans-septal approach whereby a trans-septal catheter and needle are delivered percutaneously from a point of insertion into the right femoral vein under local anesthesia. Single or biplanar flouroscopy can be used to image the trans-septal catheter during the procedure and guide the distal end of the catheter to the desired site. It is therefor advantageous for at least portions of the trans-septal catheter and LAA occluder device to be at least partially radiopaque. The trans-septal catheter is advanced through the right femoral vein into the right atrium and positioned adjacent the coronary septum. The needle is advanced from the distal end of the catheter and punctures the septum in a desired location. The trans-septal catheter is then advanced over the needle through the septum and into the left atrium. Preferably, the distal end of the trans-septal catheter or any other type of delivery catheter used for this procedure has a distal tip portion with angulation of up to about 40.degree., preferably about 10.degree. to about 30.degree. with respect to a longitudinal axis of the catheter disposed immediately proximal to the angled distal tip portion. An angled discharge axis of the distal end of the delivery catheter facilitates access to the opening of a patient's left atrial appendage. The needle assembly is then withdrawn leaving an open lumen within the trans-septal catheter with access to the left atrium. The LAA occluder device is then advanced from the proximal end of the trans-septal catheter to the distal end thereof and into or adjacent the patient's LAA. Once the occluder device is properly positioned, it can be deployed. Proper positioning of the occluder device can be determined by flouroscopy, intracavity or extracorporeal ultrasonic imaging, including transesopheogeal ultrasonic imaging (TE Echo), CT, MRI or any other suitable imaging technique.

Alternatively, the procedure to position and deploy the occluding member may be performed intraoperatively in a stand alone procedure or in conjunction with another procedure which provides access to the LAA or other desired passageway or cavity.

In another embodiment of an apparatus having features of the invention, a device for occluding a body cavity or passageway has an occlusive body configured to at least partially fill the volume of the left atrial appendage or other desired cavity or passageway of a patient. In one aspect of the invention, the occlusive body is an inflatable member which is detachably secured to a delivery catheter and configured to fit within, or preferably substantially fill the LAA of a patient. The inflatable member may also have a retention member secured to it which serves to engage the inner surface of a body cavity or passageway and maintain the position of the inflatable member relative to the body cavity or passageway. The inflatable member is configured to engage the inside surface of the LAA to prevent the passage of fluid or embolic material therefrom. Embolic material may be fluids, particulate suspended in fluids such as blood clots, gas bubbles, solid tissue or the like. In addition to or in lieu of the retention member, the inflatable member or balloon may have a ribbed surface which is shaped so as to engage the trebecula of the inside surface of a patient's LAA. The ribs should extend radially about 1 to about 4 mm from the nominal surface of the inflatable balloon, and should be spaced about 3 to about 8 mm from each other, and can be circumferential, longitudinal or spirally configured. The inflatable balloon may also include materials designed to induce fibrosis, such as Dacron-.RTM. Typically, the inflatable balloon is inflated within the LAA by injection of saline, silicone, or other suitable material.

In another aspect of the invention, the occlusive body may be a coiled member or members, in particular, one or more helical metallic coils having either a straight shape in a relaxed state or another configuration such as random, helical, convoluted shape in the relaxed state. When the coil is introduced into the cavity or passageway of the patient, it can assume the shape of a coiled mass that serves to occlude the cavity or passageway. The occlusion may result from the mechanical packing of the cavity or passageway, or may be augmented by thrombogenesis caused by the occlusive member. The coils may have a length of about 1 to about 20 cm and may have a diameter of about 0.01 to about 0.02 inches. The material from which the coils are wound can have a cross sectional dimension of about 0.001 to about 0.05 inches, preferably about 0.002 to about 0.006 inches. The occlusive coil can be made from any suitable material including stainless steel, NiTi alloy, or suitable radiopaque metals or composites such as gold, platinum, tantalum or iridium or alloys thereof. In an alternative embodiment, the occlusive coil is secured to a covering element or occluding member which is disposed in the ostium or opening of a body cavity to prevent the passage of embolic material therethrough.

In yet another aspect of the invention, the occlusive body may be a polymer mass or mass of other biocompatible material that can be introduced or injected into a body cavity or passageway, in particular, into the left atrial appendage of a patient. The polymer mass may be injected in a flowing fluid or gel form, and then harden to a non-flowing solidified or hardened mass with the passage of time or with elevated temperatures. Examples of suitable polymeric materials would include various epoxies, hydrogels, and adhesives, including polymers such as n butyl cyanoacrylate, polyisocyanate (polyurethane prepolymers), moisture curing silicone, synthetic polymers in non-aqueous but water miscible solvents (DMSO), latex, fibrin, and collagen type IV.

In general, the occlusive body would be deployed or delivered to the LAA percutaneously, as with the trans-septal approach discussed above. However, it may also be deployed intraoperatively during an invasive procedure, or ancillary to another procedure which gives access to the LAA. The occluding mass could also be secured to a covering element or barrier that is disposed within the ostium or opening of a body cavity to prevent the passage of occlusive or embolic material therethrough.

Another device having features of the invention is used to close a body cavity or LAA off permanently at its opening by pulling the opening closed and mechanically fixing the opening in a closed state. An apparatus for closing off a cavity or LAA of a patient having features of the invention generally has an elongate shaft with proximal and distal ends and a lumen within the shaft. Movably or slidably disposed within the lumen of the shaft are a plurality of tissue attachment members which also have proximal and distal ends. The tissue attachment can be accomplished by mechanical grasping or hooking, but can also be vacuum or suction actuated. The attachment by the tissue attachment members can be self activating or initiating upon contact with or penetration of tissue, or may be controlled from the proximal end of elongate members which are secured to the tissue attachment members and are also at least partially slidably disposed within the lumen of the elongate shaft. The elongate members may contain or house electrical conductors, fiber optic cables, or control lines operatively connected to the tissue attachment members to transmit the appropriate energy, signal or force to the tissue attachment members in order to initiate and maintain tissue attachment, or to collect and transmit an image of the site.

The tissue attachment members and distal ends of the elongate members attached thereto are configured to extend beyond the distal end of the elongate shaft which can be positioned adjacent to tissue to be closed off. In this way, the tissue attachment members can extend distally and at an angle to a longitudinal axis of the elongate shaft and make contact with tissue and attach thereto. The tissue attachment members may then be retracted into the distal end of the elongate shaft so as to pull the various portions of the tissue together and close the cavity or opening of the LAA. The device preferably includes a closure member which is generally configured as a retaining ring which is slidably disposed over the elongate members and configured to restrain tissue collected and pulled together by the tissue attachment members upon retraction. The closure member may also be a staple which secures the tissue of the opening. The tissue of the annular edge of the cavity which has been collected and pulled together by the tissue attachment members may also be fixed or secured in the closed state by suturing, bonding with a biocompatible polymer adhesive, stapling, tissue welding or the like. Tissue welding suitable for use with the invention may be carried out with laser energy applied to the closed tissue. Laser energy may be supplied by Nd:YAG or HO:YAG laser types. Various configurations of surgical staples could be used to fix or secure the closed tissue of the body cavity or LAA, including the type disclosed by U.S. Pat. No. 4,603,693 to Conta et al. which is incorporated by reference herein in its entirety and which discloses a device for deploying surgical staples.

The apparatus for closing a body cavity is generally delivered in a non-invasive, preferably percutaneous manner. An elongate delivery catheter having an inner lumen is percutaneously delivered such that a distal end of the delivery catheter is adjacent the opening of the patient's body cavity to be closed off. The closure device or apparatus for closing off a cavity or LAA of a patient is advanced distally within the delivery catheter from the proximal end thereof. The closure device is then advanced out of the distal end of the delivery catheter, and the tissue attachment members and elongate members advanced distally from the elongate shaft so that the tissue attachment members are in contact with the tissue of the opening of the body cavity to be closed. The tissue attachment members are then activated so as to attach to the tissue. The tissue attachment members are then retracted proximally back into the elongate shaft and the closure member advanced distally, preferably by distal movement of an elongate push shaft disposed proximal to the closure member and slidably disposed over the elongate members of the closure device. The closure member is advanced until it is disposed over the tissue of the cavity opening that is attached to the tissue attachment members and confines the tissue of the cavity opening so as to close off the cavity. The tissue attachment members can then be deactivated and withdrawn, and the closure device and delivery catheter withdrawn proximally to complete the procedure.

These and other advantages of the invention will become more apparent from the following detailed description when taken in conjunction with the accompanying exemplary drawings.

BRIEF DESCRIPTION OF THE DRAWINGS

FIG. 6 shows a perspective view of an apparatus for sealing off a body cavity having features of the invention.

FIG. 7 shows an elevational view in partial section of an apparatus for sealing off a body cavity having features of the invention.

FIG. 8 shows a transverse cross-sectional view of the apparatus of FIG. 7 taken along lines 8-8.

FIG. 9 shows a schematic view of a patient's heart with a trans-septal catheter deployed through the septum and a delivery catheter and apparatus for sealing off a body cavity disposed therein.

DETAILED DESCRIPTION

Figure 1:
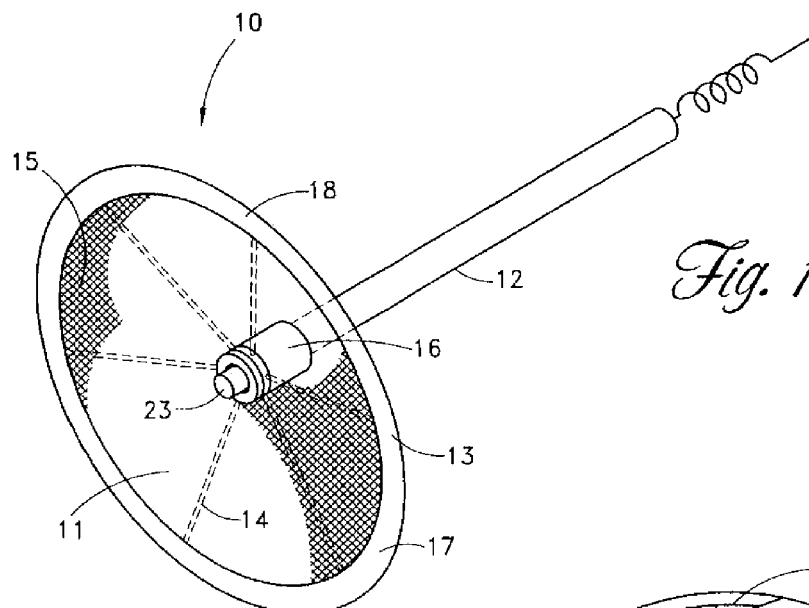
FIG. 1 shows a perspective view of an embodiment having features of the invention with an occluding member and a retention member.
Figure 2:
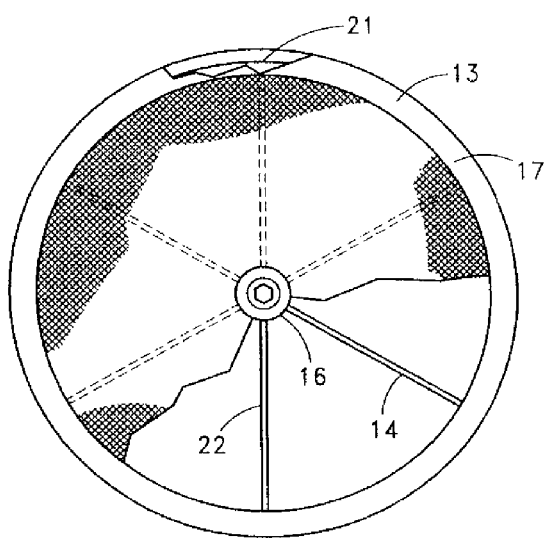
FIG. 2 shows an end view of the apparatus of FIG. 1 in partial section.
Figure 3:
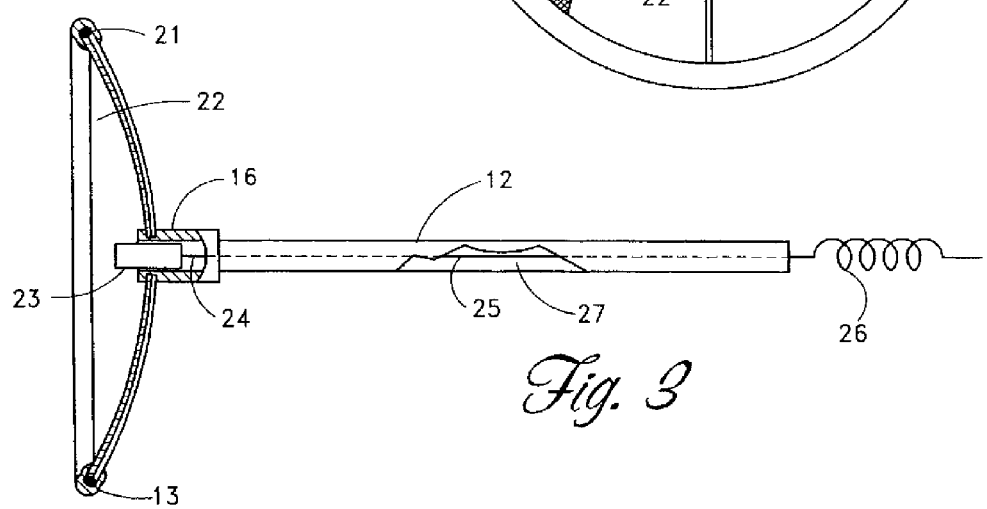
FIG. 3 shows a longitudinal cross sectional view of the apparatus of FIGS. 1 and 2.

FIGS. 1-3 show an embodiment of an occluding device 10 having features of the invention where an occluding member 11 is secured to a retention member 12 that is arranged to fix the occluding member in a desired position within a body passageway or cavity. The occluding member 11 generally has disc shape with an outer rim 13 around the perimeter of a frame structure 14 which supports a barrier 15. The outer rim 13 can be circular or polygonal, or any other shape that is suitable for conforming to the inside surface of a body cavity. A hub 16 can be located near the center of the occluding member 11 which serves to connect the retention member 12 to the occluding member, in addition to other functions. The outer rim 13 is typically made from a soft polymer material 17 which permits flexibility of the outer rim and facilitates sealing of the outer rim against the inside surface of a body cavity or passageway. The barrier 15 can be a thin mesh or film of material which serves to block the passage of material within an area surrounded by the outer rim 13. The barrier 15 can be secured to the outer rim 13 along its entire perimeter 18 in order to achieve a complete seal therebetween and can be molded into the outer rim 13 or bonded thereto by a suitable method such as gluing, welding, sewing or other suitable method. The outer rim 13 is at least partially supported by the frame structure 14 which connects the outer rim and the hub. The frame structure 14 can be made from one or more elements of high strength material such as stainless steel or MP35N, or may preferably be made from shape memory or pseudoelastic alloys such as NiTi. Preferably, the frame structure 14 is made from a material which can be self expanding from a constrained configuration so that the occluding device 10 can be delivered to the deployment site in a low profile an flexible configuration which facilitates percutaneous delivery. Preferably a radial hoop 21 is contained within the soft polymer material 17 of the outer rim 13 and serves to maintain the annular shape of the outer rim and facilitate radial expansion of the outer rim from a constrained position or configuration. The radial hoop 21 may be isolated within the soft polymer material 17 of the outer rim 13, or may be connected to at least some the elements 22 of the frame structure 14, in order to have stronger mechanical joint between the outer rim and the frame structure. The radial hoop 21 is shown in a substantially circular configuration, but may also be polygonal or otherwise suitably shared, and may have connections or joints spaced thereon to facilitate contraction or folding of the device for non-invasive delivery.

In addition to connecting the retention member 12 and the occluding member 11, the hub 16 may serve to house a rotational coupling 23 which is connected to the proximal end 24 of a tissue penetrating shaft 25 within the retention member. The rotational coupling 23 allows the transfer of torque to the tissue penetrating shaft 25 which preferably has a helically shaped extension or distal extremity 26 which is configured to screw into tissue and be mechanically fixed thereto. Longitudinal movement of the tissue penetrating shaft 25 relative to the retention member 12 and hub 16 may be prevented by sizing a lumen 27 of the retention member which contains the tissue penetrating shaft such that the helically shaped extension 26 at the distal end is too large to pass through the lumen and the proximal end 24 of the tissue penetrating shaft is prevented from passing through the lumen by the rotational coupling attached thereto. The rotational coupling 23 may also be configured to be longitudinally captured by the hub 16 but still be rotatably disposed therein.

Figure 3A:
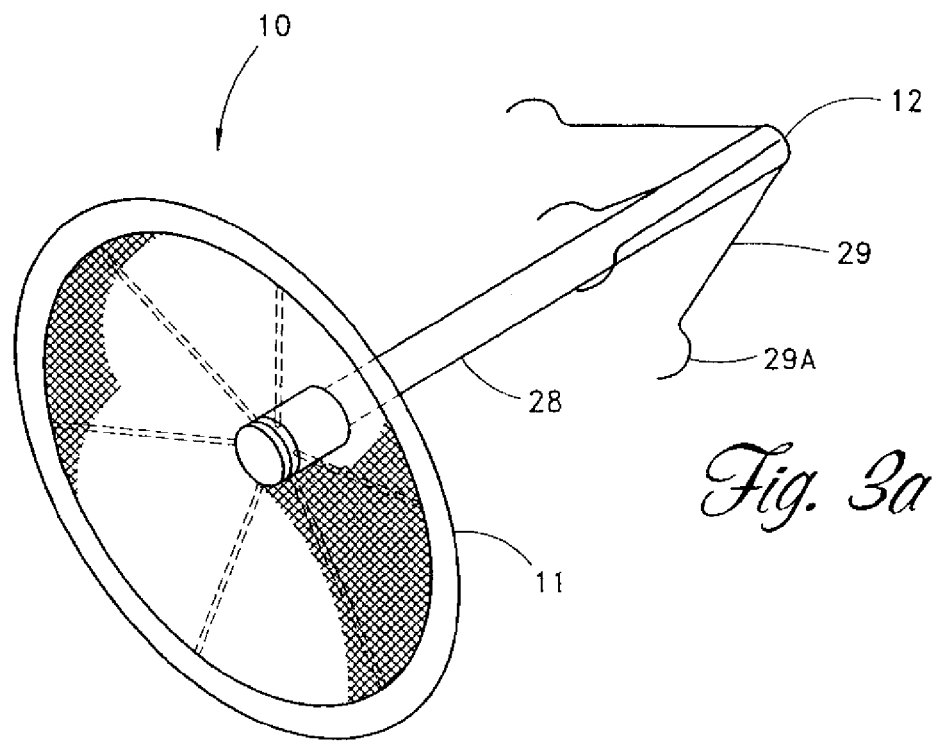
FIG. 3A shows a perspective view of an apparatus having features of the invention.
Figure 3B:
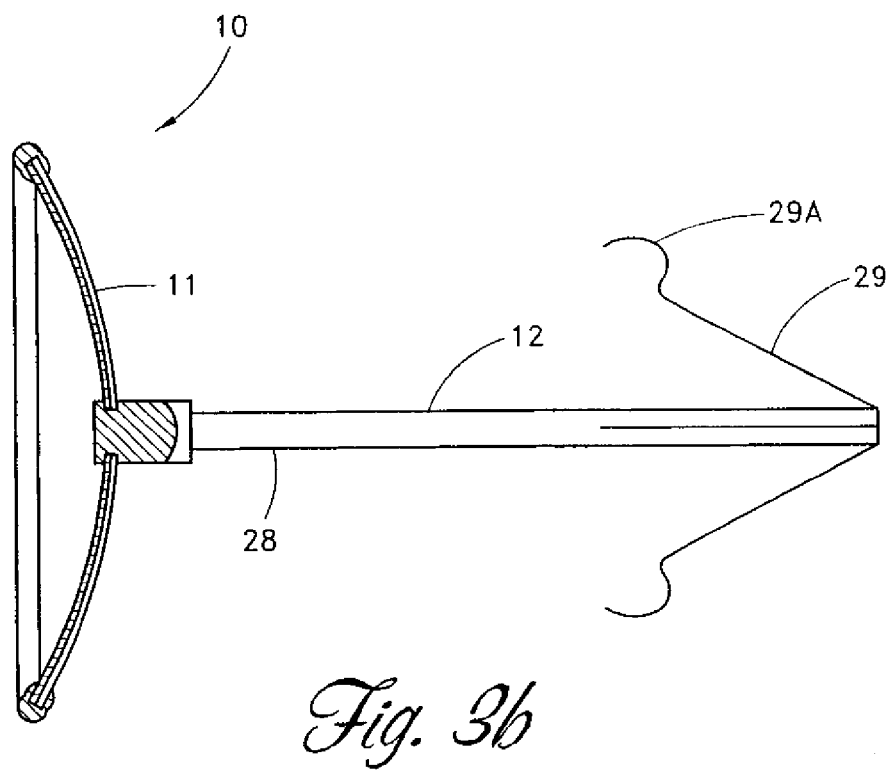
FIG. 3B shows an elevational view in partial section of the apparatus of FIG. 3A.

FIGS. 3A and 3B depict an alternative embodiment of an occluding device 10 having an occluding member 11 and a retention member 12. The retention member 12 has a shaft 28 and radially extending members 29 extending radially from a proximal end of the shaft. The radially extending members 29 serve to anchor the shaft 28 and the occluding member 11 by engaging the tissue surrounding the occluding device. Preferably, the radially extending members are self expanding from a constricted state and are made of a pseudo elastic alloy such as NiTi, or a high strength material such as stainless steel. Although it is preferable for the radially extending members 29 to be self expanding from a constricted state, they may also be expanded by use of shape memory properties or a radial outward force as would be provided by an inflatable balloon or the like. The shaft 28 can be a single element or made of multiple elements, and can be made from the same materials as the radially extending members or different materials such as polymers or polymer composites. The radially extending members 29 have a proximally directed bias at their radial extremities 29A so that the members readily fold down and move easily in a distal direction during insertion of the occluding device 10, but spring outward and aggressively engage surrounding tissue upon movement in a proximal direction. This configuration of the radially extending members 29 allows easy insertion into a body cavity, but prevents egress of the device 10 in and outward or proximal direction.

Figure 4:
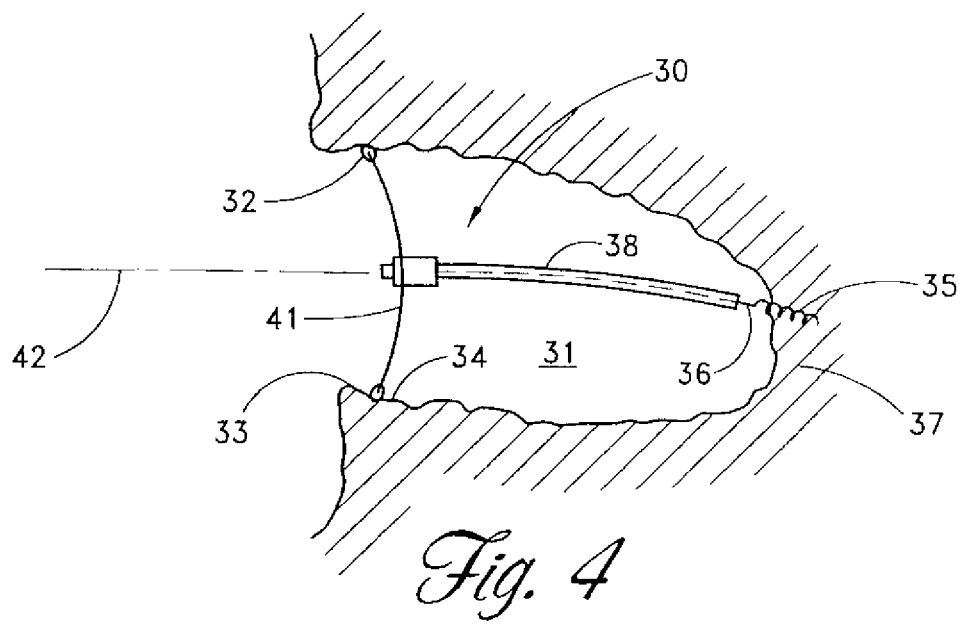
FIG. 4 shows an elevational view of an apparatus having features of the invention in a deployed state within a body cavity.

FIG. 4 depicts an occluding device 30 similar to that depicted in FIGS. 1-3 deployed within the left atrial appendage 31 of a patient. An outer rim or periphery 32 of the occluding device 30 is disposed adjacent the opening 33 of the left atrial appendage 31 in a position which allows for a substantial seal of the outer rim against the inside surface 34 of the LAA. A helically shaped distal extremity 35 of a tissue penetrating shaft 36 has been screwed into the wall tissue of the LAA and is mechanically secured thereto. A retention member 38 maintains the position of an occluding member 41 in a substantially perpendicular orientation with respect to a longitudinal axis of the LAA 42.

Figure 5:
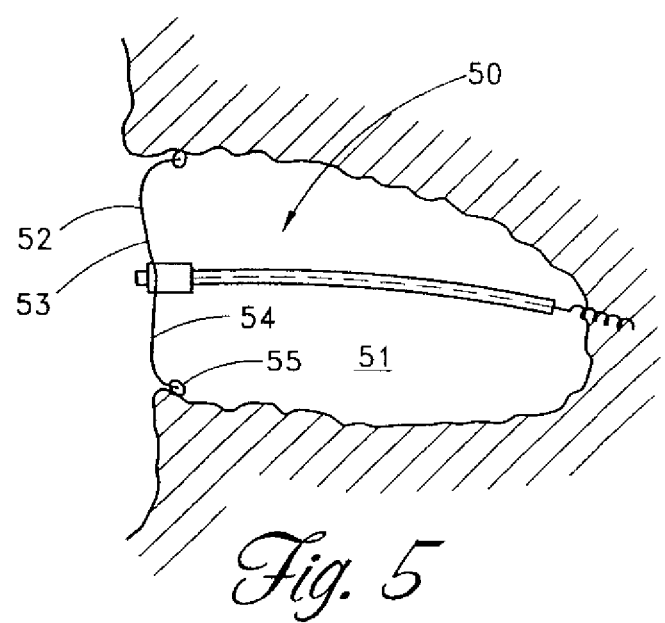
FIG. 5 shows an elevational view of an apparatus having features of the invention in a deployed state within a body cavity.

FIG. 5 depicts an occluding device similar to that depicted in FIGS. 1-4 deployed within a LAA 51 of a patient similar to what is shown in FIG. 4. The structure of an occluding member 52 of the embodiment as shown in FIG. 5 differs from that shown in FIG. 4 in that a barrier 53 and frame structure 54 of the embodiment of FIG. 5 protrudes proximally from a plane defined by an outer rim 55. This configuration may be useful for certain morphologies of patient's LAAs. One object of the invention is to create a smooth surface outside the body passageway or cavity in order to prevent turbulent flow or eddies of blood or other bodily fluid within the cavity or passageway. The alternative configuration of the occluding device 50 shown in FIG. 5 may be useful in this regard.

FIG. 6 shows an alternative embodiment of an occluding device 60 which has an occluding member 61, a frame structure 62, a barrier 63 and a retention member in the form of an expandable member 65 which has linked elements 66 that are preferably expandable from a constrained configuration. The expandable member 65 is generally cylindrical in shape and can have a series of circumferential linked elements 66 connected by links 68. Although FIG. 6 depicts the expandable member 65 as a series of linked elements 66, those skilled in the art will realize that a similar effect can be achieved with a single wire in a helical configuration or a plurality of wires in a mesh or braided configuration, or any other suitable configuration that can be self expanding from a constrained configuration or expanding with the application of heat or other form of energy or force. For example, the expandable member 65 may be configured to be deployed by an outward radial force delivered from within the expandable member. An inflatable balloon or the like could be used to exert such a force. The expandable member is preferably secured to an outer rim 71 of the occluding member 61 but may also be secured to the frame structure 62 directly or indirectly. The expandable member 65 can be self expanding from a constrained configuration as can the occluding member 61 and the frame structure 62 and outer rim 71 thereof. The frame structure 62, outer rim 71 and barrier 63 may have construction similar to that described above with regard to the similar elements of the embodiments depicted in FIGS. 1-5.

Referring to FIG. 7, the expandable member 65 as shown in FIG. 6 may also have a sheath 72 disposed around it so as to act as a shield between the expandable member and an inner surface of a patient's body cavity or passageway. The sheath 72 may facilitate the sealing function of the occluding member 61, but is primarily intended to prevent damage to either tissue on the inside surface of a body cavity or to the linked elements 66 of the expandable member. The sheath 72 may surround all or part of the expandable member 65 and may be made from a variety of suitable biocompatible materials such as Dacron.RTM., Nylon, TFE, PTFE or ePTFE. The sheath 72 may be a weave, braid, film or have any other suitable configuration. Expandable member 65 may also be coated by dipping, spraying, or other suitable process with a friction reducing material such as Teflon.RTM., or with an active compound such as heparin.

FIG. 8 shows a transverse cross sectional view of the embodiment of FIG. 7 taken at lines 8-8. The frame structure 62 has an axis or hub 73 disposed at approximately the center of the frame structure which serves to connect the various radial elements 74 of the frame structure. The hub 73 can have an independent structure that links the several elements 74 of the frame structure 62 or it may be merely the terminus of the various frame structure elements and have a solid composition. In either structure, the hub 73 preferably allows a constrained configuration of the occluding member 61 to facilitate percutaneous delivery of the occluding device 60. The hub 73 may also have a lumen disposed therein to allow passage of a guidewire of other guiding member. Preferably, the lumen would have a self sealing valve or gasket which prevents the passage of fluid or embolic material once the guidewire or guiding member is removed from the lumen.

Referring to FIG. 9, a schematic view of a patient's heart 80 in partial section shows a trans-septal catheter 81 having a proximal end 82 and a distal end 83. The distal end 83 of the trans-septal catheter 81 is disposed within a patient's heart 80 with the distal end 84 of a delivery catheter 85 extending from the distal end 83 of the trans-septal catheter. The distal end 83 of the trans-septal catheter 81 has breached the septum 86 of the patient's heart 80 and is disposed adjacent the opening of the patient's LAA 88. At the proximal end 82 of the trans-septal catheter 81 there is a Luer connector 91 coupled to a hemostasis valve 92 which prevents the egress of blood from a lumen 93 of the trans-septal catheter 81. The proximal end 94 of the delivery catheter 85 extends proximally from the hemostasis valve 92 and has a Luer connector 95 attached to the proximal extremity thereof. The proximal end 96 of a plunger 97 extends from the Luer connector 95 of the delivery catheter. The proximal end 94 of the delivery catheter is arranged to allow rotational and axial movement of the plunger 97 while preventing blood or other bodily fluids from leaking between the delivery catheter 85 and the plunger 97.

Figure 10:
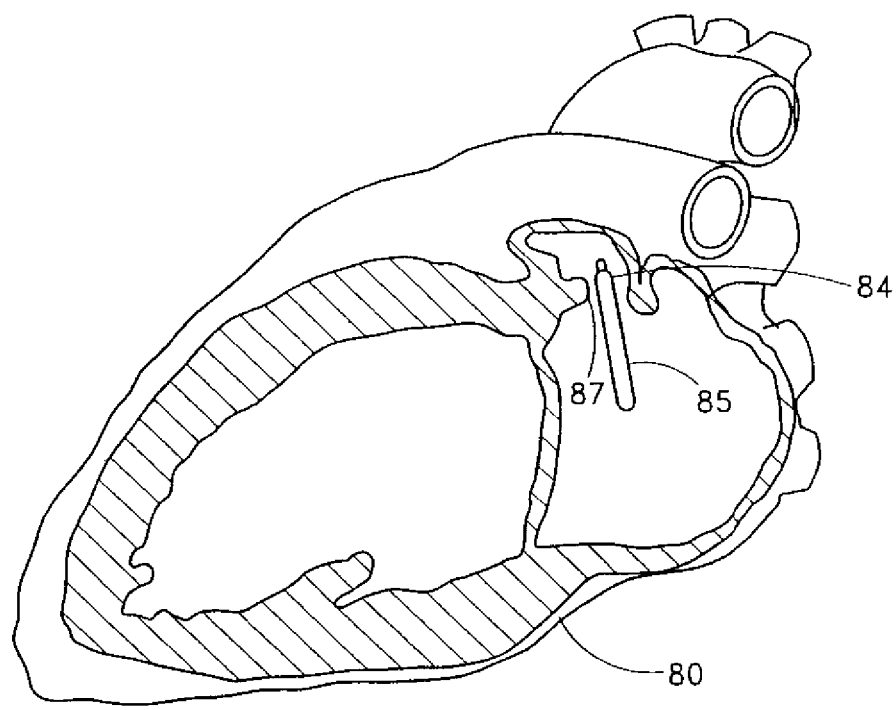
FIG. 10 shows a schematic view of a patient's heart in partial section with a delivery catheter disposed within the opening of the LAA.
Figure 11:
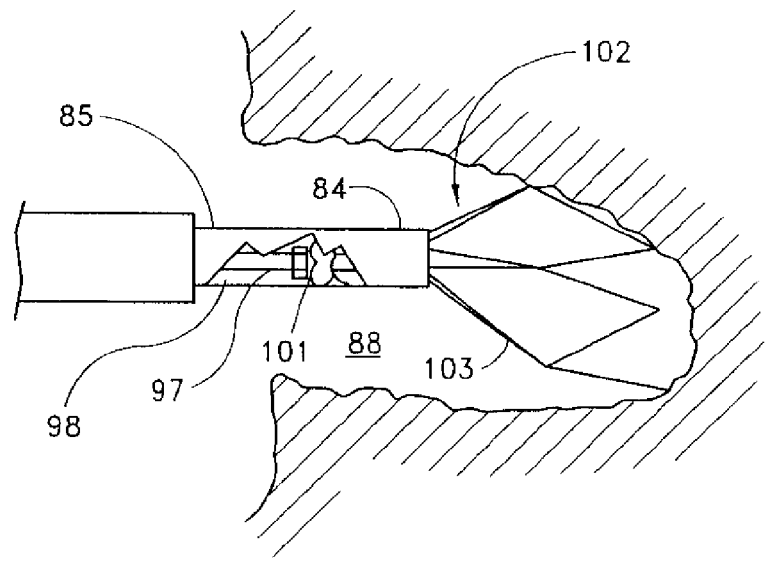
FIG. 11 shows a magnified view of the delivery catheter distal end and the LAA of a patient of FIG. 10 with an apparatus for sealing off a body cavity partially deployed within the LAA.

Referring to FIG. 10, a patient's heart 80 is shown in partial section with the distal end 84 of a delivery catheter 85 disposed within the LAA opening 87. FIG. 11 is a magnified view of the LAA 88 shown in FIG. 10 and the distal end of the delivery catheter 84, which is shown in partial section, contains a plunger 97 which is slidably disposed within an inner lumen 98 of the delivery catheter 85 and serves to apply axial force in a distal direction on the collapsed occluding member 101 disposed within the delivery catheter so as to force the occluding device 102 from the delivery catheter and deploy it. An occluding device 102 having an expandable member 103 and an occluding member 101 secured thereto is partially deployed and extending from the distal end of the delivery catheter 84 into the patient's LAA 88. The occluding device 102 can also be guided into the patient's LAA 88 by use of an appropriate guidewire or guiding member.

Figure 12:
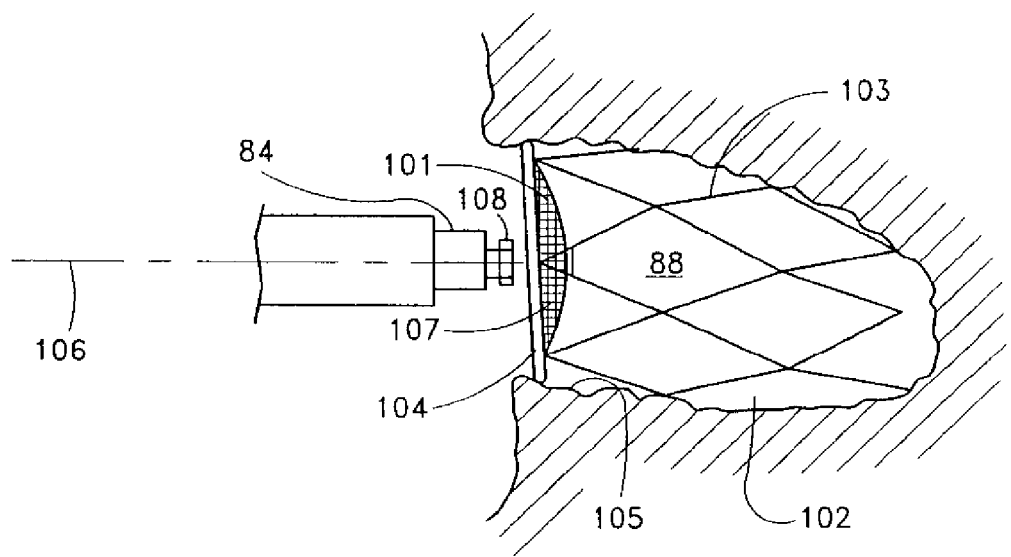
FIG. 12 shows the apparatus for sealing off a body cavity of FIG. 11 fully deployed within a LAA.

FIG. 12 shows the occluding device 102 of FIG. 11 in a deployed state within the patient's LAA 88. An outer rim 104 of the occluding member 101 is in substantial sealing contact with the inside surface 105 of the LAA 88. The expandable member 103 has expanded so as to contact the inside surface 105 of the LAA and secure the occluding device 102 thereto and maintain the occluding member 101 in a substantially perpendicular orientation relative to a longitudinal axis 106 of the LAA 88. A barrier 107 is disposed within an area bounded by the outer rim 104 and is positioned to prevent the passage of embolic or other material to or from the LAA 88. The distal end 108 of the plunger 97 is extending from the distal end of the delivery catheter 84 after having pushed the occluding device 102 from the delivery catheter.

Figure 13:
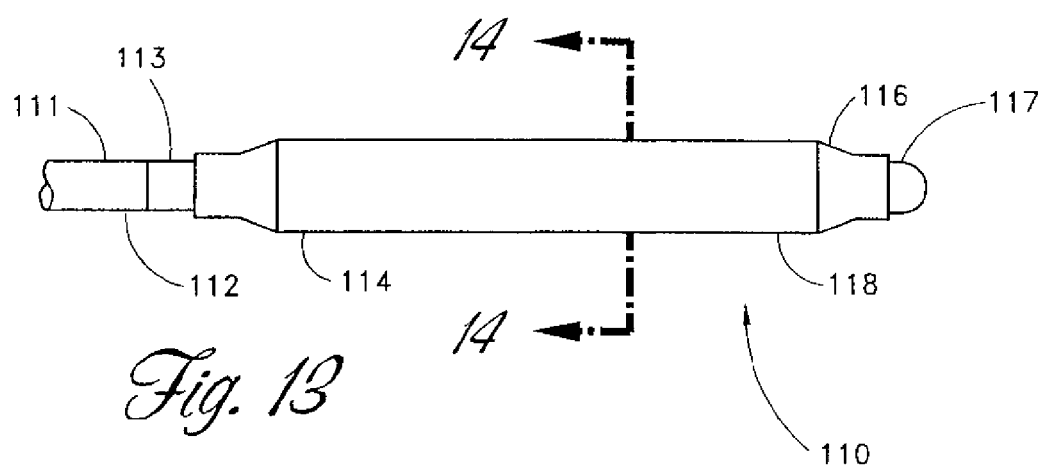
FIG. 13 shows an elevational view of a device for occluding a body cavity having features of the invention.

Referring to FIG. 13, an occluding device 110 having features of the invention is shown. The occluding device 110 has a delivery catheter 111 with a distal end 112, a detachment mechanism 113 disposed on the distal end of the delivery catheter and an occlusive body or inflatable member 114 detachably secured to the detachment mechanism. The inflatable member 114 has a proximal end 115 and a distal end 116 with the proximal end being attached to the detachment mechanism 113 and the distal end terminating at an end cap 117. The inflatable member 114 has an outside surface 118 that may contain a fibrosis inducing material such as Dacron-.RTM. or other similar materials. The inflatable member 114 may be made from a fluid tight film of polymer material which can be either compliant or non-compliant. Preferably the inflatable member 114 is made from silicone, however, any suitable material such as polyethylene, polyurethane or PET can be used.

The detachment mechanism 113 can be activated by mechanical force or by delivery of thermal or optical energy by a suitable conduit. Alternatively, the inflatable member can be pushed into the LAA from the delivery catheter 111 by an elongate push member without the use of a detachment mechanism. The inflatable member 114 can be filled with a gas, fluid or gel which is injected under pressure through the delivery catheter 114 and into the inflatable member. Suitable fluids to inject would include saline and silicone. The inflatable member 114 may also be filled with a polymer material that can be hardened. A fluid, gel or polymer used to fill the inflatable member may contain contrast agents such as gold, tantalum, bismuth, barium sulfate or the like in order to improve visualization under flouroscopy or x-ray imaging.

Figure 14:
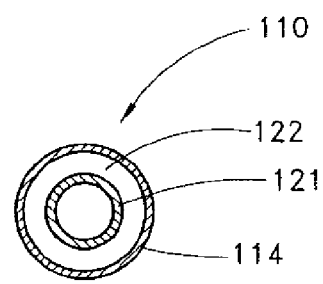
FIG. 14 shows a transverse cross sectional view of the device for occluding a body cavity of FIG. 13 taken along lines 14-14.

FIG. 14 is a transverse cross sectional view of the occluding device 110 of FIG. 13 taken along lines 14-14. An optional inner shaft 121 is shown disposed within the inflatable member 114, preferably in a concentric arrangement. The inner shaft 121 provides longitudinal axial support to the inflatable member 114 so as to maintain a longitudinal dimension of the inflatable member 114 when it is being inflated and deployed. The inner shaft 121 may be solid or contain one or more lumens that may or may not be in fluid communication with an inner lumen 122 of the inflatable member 114, and can be used for the passage of a guidewire or guiding member.

Figure 15:
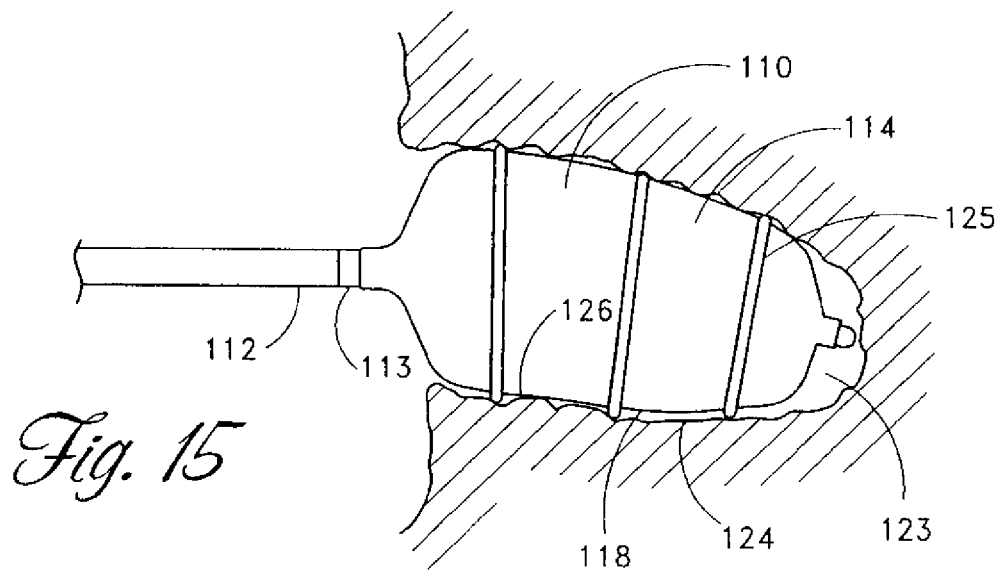
FIG. 15 shows a device for occluding a body cavity having features of the invention deployed within a LAA.

FIG. 15 depicts an alternative embodiment of an occluding device 110 which consists of an inflatable member 114 similar to the inflatable member of FIG. 13, shown substantially deployed, within a patient's LAA 123. The inflatable member 114 has been at least partially filled with a fluid, gas or gel within the patient's LAA 123 such that the outside surface of the inflatable member 118 is in contact with at least part of the inside surface 124 of the LAA. The inflatable member 114 can have rib members 125 which can mechanically interlock with the trebeculae 126 of the inside surface of the LAA 124 or other surface irregularities of the inside surface of a patient's body cavity or passageway. The rib members 125 form a complete circumference of the inflatable member 114, but could also form a partial circumference, spiral configuration, or consist of random projections on the surface of the inflatable member 118. The rib members 125 should extend radially about 1 to about 4 mm from the nominal surface of the inflatable member 114, and are preferably spaced about 3 to about 8 mm from each other. The rib members 125 may be made from any suitable polymer material, but are preferably made from the same material as the inflatable member, and are integrally molded thereon, or bonded thereto with a heat weld or adhesive bond suitable for bonding flexibly medical polymers. The inflatable member 114 is depicted with the distal end of the delivery catheter 112 and detachment mechanism 113 attached. As an alternative, or in addition to the polymer rib members 125 shown in FIG. 15, barbs or hooks could be secured to the outside surface of the inflatable member 114 which are configured to engage the inside surface of a patient's LAA 124. Preferably, barbs or hooks disposed on the outside surface of the inflatable member and configured to engage the tissue of the inside surface of a patient's LAA 124 would have a proximally directed bias at their radial extremity so that the barbs would fold down and move easily in a distal direction during insertion of the inflatable member 114, but would spring outward and aggressively engage the tissue of the body cavity upon movement in a proximal direction of the inflatable member.

Figure 16:
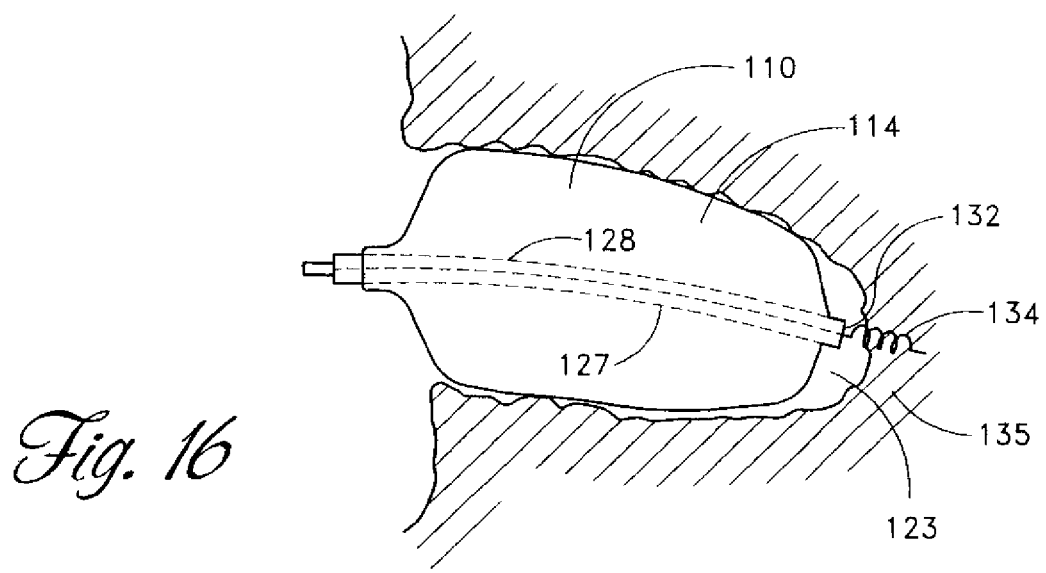
FIG. 16 shows a device for occluding a body cavity having features of the invention deployed within a LAA.

FIG. 16 depicts an occluding device 110 consisting of an inflatable member 114 which is shown deployed within a patient's LAA 123. The embodiment of the inflatable member 114 shown in FIG. 16 has an optional retention member 127 with a tissue penetrating shaft 128 which has a proximal 131 end and a distal end 132. A rotational coupling 133 is disposed at the proximal end 131 of the tissue penetrating shaft 128 and a helically shaped extremity 134 is disposed at the distal end of the shaft 132. The helically shaped distal extremity 134 is shown deployed within and mechanically engaging wall tissue 135 of the LAA so as to secure the inflatable member 114 and maintain its position within the LAA 123 of the patient.

Figure 17:
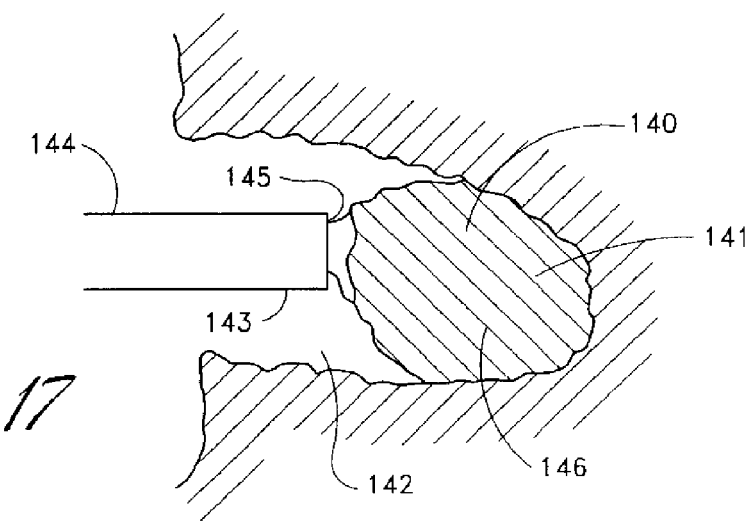
FIG. 17 shows a LAA being occluded by a method having features of the invention.

FIG. 17 shows an alternative embodiment of an occlusive member 140 consisting of a polymer mass 141 which has been injected or delivered into a patient's LAA 142. The distal end 143 of a delivery catheter 144 has a lumen 145 therein which extends to a proximal end of the delivery catheter which is in fluid communication with a source of pressurized polymer material. A source of pressurized polymer material 146 can be any type of pump or device capable of forcing a polymer fluid or gel into the proximal end of the delivery catheter with sufficient pressure to force the polymer fluid or gel out the distal end 143 of the delivery catheter 144 and into a patient's body cavity or passageway. The delivery catheter 144 may be positioned by the techniques discussed above, e.g. the Mullins trans-septal approach or any other suitable method. Once the distal end of the delivery catheter 143 is disposed within a desired portion of the patient's LAA 142, the polymer mass 141 may be injected to fill the cavity to the desired level. The LAA 142 can be completely or partially filled with the polymer mass 141 which can be formulated to harden over time, with heat or remain in a fluid or gel state. The distal end of the delivery catheter can optionally include an expandable member which is used to substantially seal the delivery catheter against the inside surface of the opening of the patient's body cavity during the delivery of polymer material. The expandable member can be an inflatable balloon or the like which are well known in the art.

Optionally, a retention member 127 having a tissue penetrating shaft 128 or the like, such as shown in FIG. 16 with regard to the inflatable member 114, may be deployed within the LAA 142 prior to injection of the polymer mass 141 and captured thereby so as to secure the polymer mass within the LAA. Alternatively, the polymer mass can be used to fill the patient's LAA and surround and secure a deployed device as shown in FIG. 4 or 5 in the patient's LAA 142.

Figure 18:
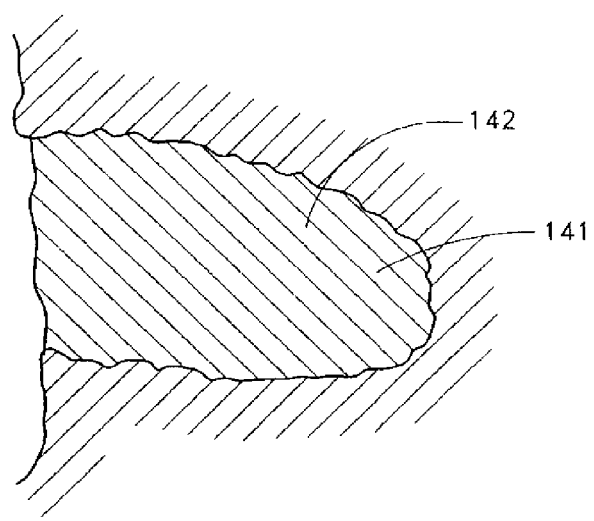
FIG. 18 shows a LAA occluded by method having features of the invention.

Once a desired amount of polymer mass 141 has been injected into the LAA 142, as assessed for example by TE Echo imaging, the delivery catheter 144 may be withdrawn and the procedure terminated. Preferably the entire LAA 142 of a patient is filled with the polymer mass 141 as shown in FIG. 18 and hardens or gels to maintain its shape. It may be desirable to have the polymer mass 141 retain a soft compressible form after setting or hardening so that it is at least partially compliant with the constrictive pumping action of a heart and resistant to fatigue as a result thereof. A material used to form the polymer mass 141 may contain contrast agents such as gold, platinum, tantalum, bismuth or the like in order to better visualize the deployment of the polymer mass under fluoroscopic or x-ray imaging.

Figure 19:
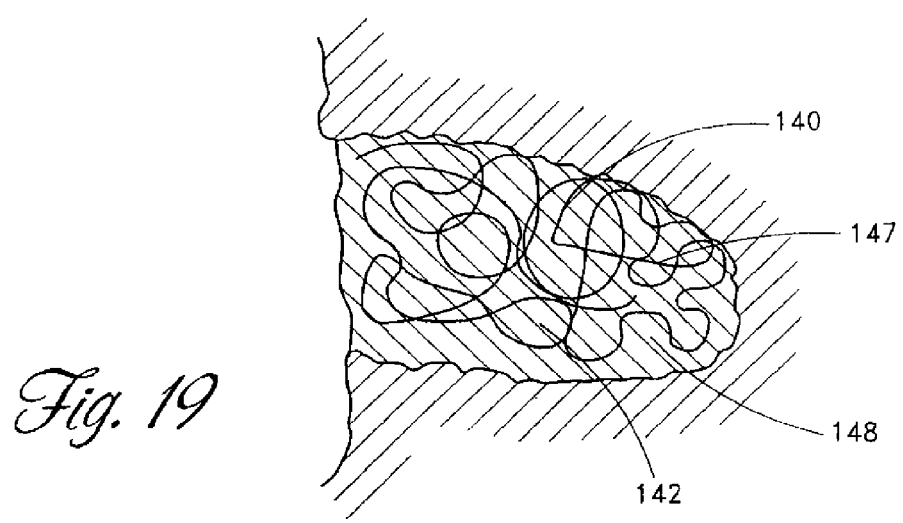
FIG. 19 shows a LAA occluded by method having features of the invention.

Another alternative embodiment of an occlusive member 140 can be found in FIG. 19 which shows an occlusive coil 147 which has been deployed within an LAA 142 The occlusive coil 147 as shown has assumed a random configuration that is mechanically occluding the LAA 142 and which has induced clot and or fibrosis formation 148 which further facilitates occlusion of the LAA 142.

Figure 20:
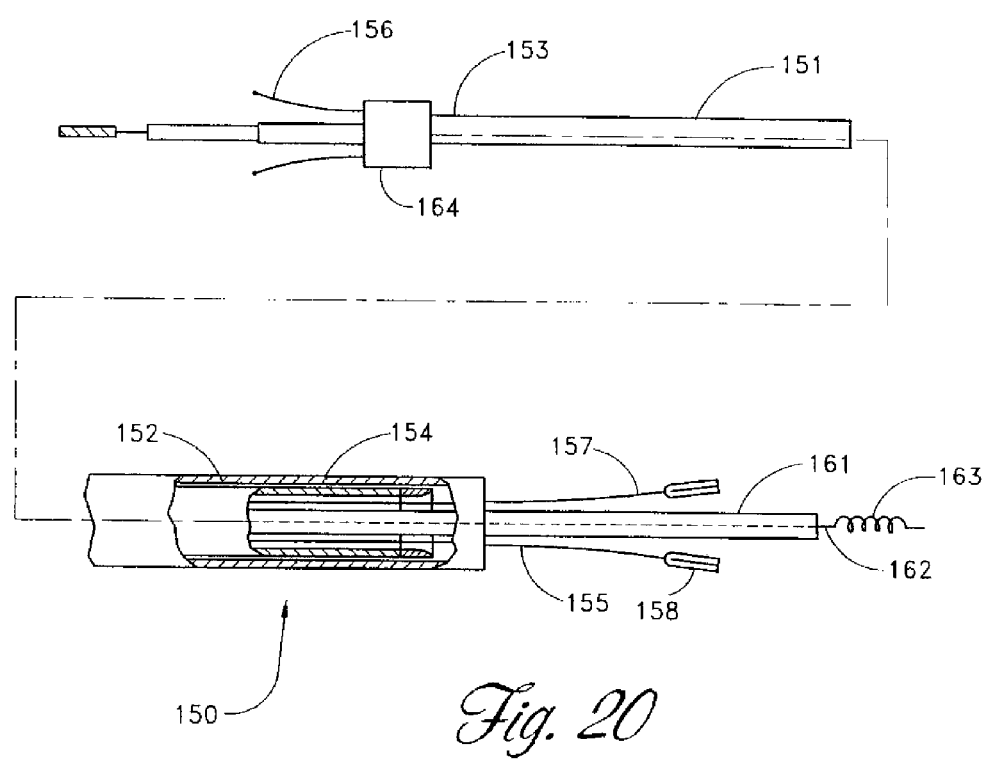
FIG. 20 is an elevational view of an apparatus for closing an interior body cavity of a patient in partial section having features of the invention.

An apparatus for closing off a body cavity or passageway 150 is shown in FIG. 20 which has features of the present invention. The apparatus 150 has an elongate shaft 151 with an inner lumen 152 and a proximal end 153 and a distal end 154. Slidably disposed within the inner lumen 152 of the elongate shaft 151 are at least two elongate members 155 which have proximal ends 156 and distal ends 157 and have tissue attachment members 158 disposed on the distal ends. An optional distal anchor member 161 is also slidably disposed within the inner lumen 152 of the elongate shaft 151 and preferably has a distal end 162 terminating with a helical member 163. The proximal end 153 of the elongate shaft 151 has a proximal control module 164 which seals the inner lumen 152 of the elongate shaft 151 and allows rotation and translation of the proximal ends 156 of the elongate members 155 and the distal anchor member 161 while maintaining a seal between said members to prevent leakage of bodily fluids therefrom. The proximal control module 164 can optionally be configured to control advancement and retraction of the elongate members 155 and control activation of the tissue attachment members 158.

Figure 21:
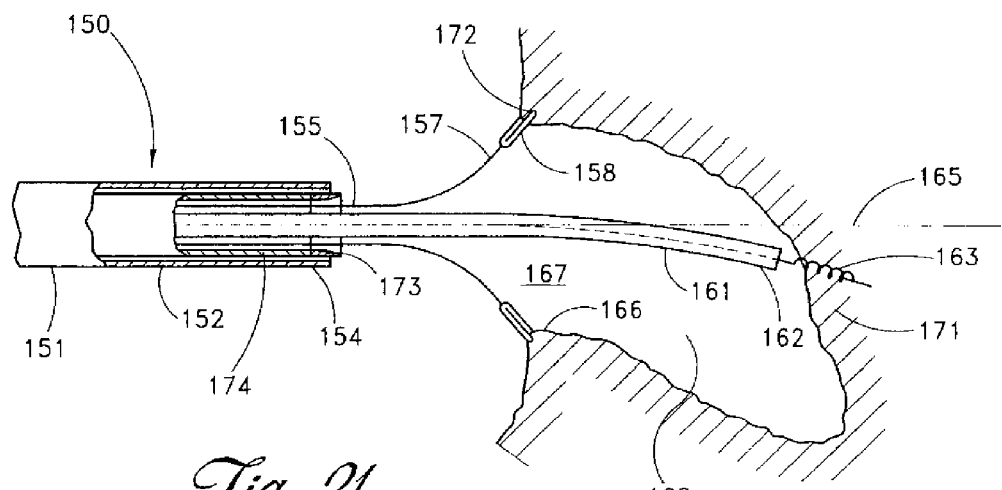
FIG. 21 is a schematic view of an apparatus for closing an interior body cavity of a patient in contact with tissue of a LAA.
Figure 22:
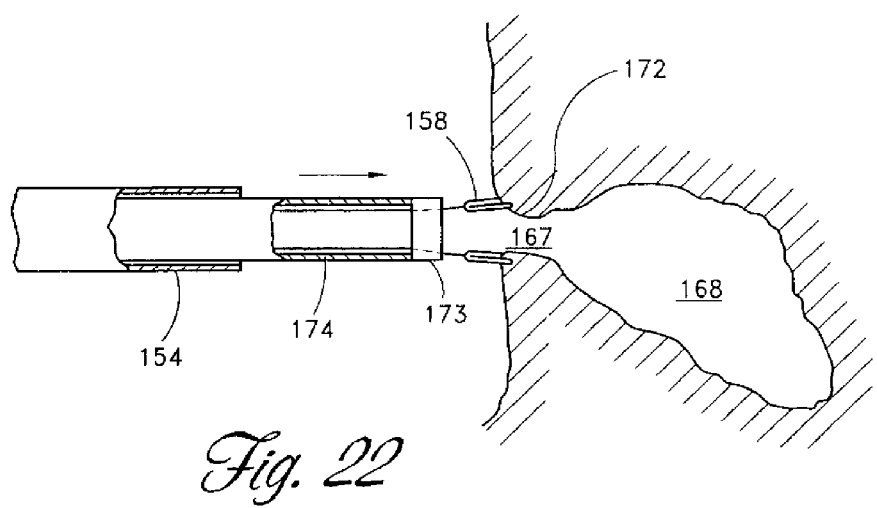
FIG. 22 is a schematic view of an apparatus for closing an interior body cavity of a patient in contact with tissue of a LAA.
Figure 23:
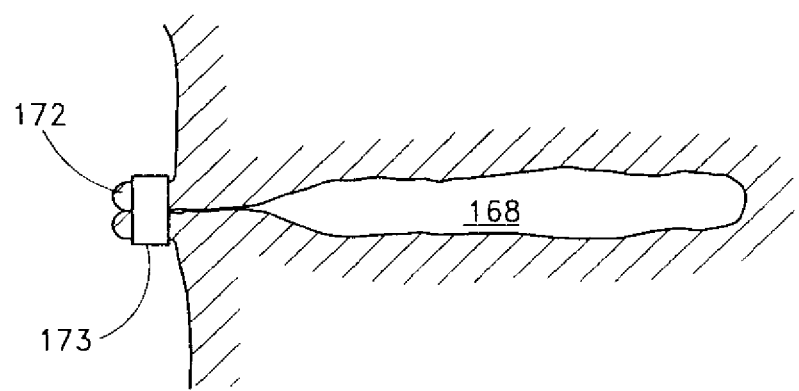
FIG. 23 shows a LAA which has been closed by a method having features of the invention.

FIG. 21 shows the apparatus for closing off a body cavity 150 of FIG. 20 with the distal ends of the elongate members 157 and the tissue attachment members 158 extending distally from the distal end of the elongate shaft 154. The distal ends of the elongate members 157 are angled or deflected from a longitudinal axis 165 of the elongate shaft 151 so as to engage tissue 166 of the opening 167 of the LAA 168 as shown. The elongate members 155 may be deflected by an abutment or angulation contained in the distal end of the elongate shaft 154, but are preferably preshaped in an angled configuration which manifests when the distal ends are freed of the constraint of the inner lumen 152 of the elongate shaft an allowed to assume their relaxed preshaped condition. The helical member 163 at the distal end 162 of the distal anchor member 161 is engaged with the wall tissue 171 of the LAA 168 so as to provide an optional anchor that can be used to move the elongate shaft 151 relative to the distal anchor member 161 and give greater control of the longitudinal axial movement of the elongate shaft relative to the LAA opening 167. The tissue attachment members 158 are shown attached to the annular edge 172 of the LAA opening 167. Once the tissue attachment members 158 are attached, a closure member or retaining ring 173 may be advanced distally by applying axial force on an elongate push shaft 174 which draws the tissue attachment members 158 and the tissue attached thereto closer together as shown in FIG. 22. As the closure member 173 is further advanced distally, the annular edge of the LAA 172 is drawn closed, and eventually, the annular edge of the LAA will be completely closed into a closed state with the closure member 173 surrounding and compressing the tissue of the annular edge as shown in FIG. 23. Once a closed state of the LAA is achieved, the tissue attachment members 158 may be detached, and the apparatus for closing off a body cavity 150 withdrawn. One alternative method can have the tissue attachment members 158 drawn together by retracting them proximally into the distal end 154 of the elongate shaft 151 as opposed to distally advancing the closure member 173 with the elongate push shaft 174. In this way, the annular edge of the LAA 172 can be drawn into a closed state within the distal end 154 of the elongate shaft 151 at which point the annular edge may be fixed in the closed state by a variety of methods including suturing, tissue welding, the application of a suitable biocompatible adhesive, surgical staples or the like.

While particular forms of the invention have been described, it will be apparent that various modifications can be made without departing from the spirit and scope of the invention. Accordingly, it is not intended that the invention be limited, except as by the appended claims.

What is claimed is:

1. A method of preventing passage of embolic material from a left atrial appendage, comprising:
   advancing a catheter having a proximal end and a distal end through the patient until the distal end is disposed adjacent the opening of the patient's left atrial appendage; and
   releasing a device from the distal end of the catheter to deploy the device within the left atrial appendage, the device configured to block an opening to the left atrial appendage to prevent passage of embolic material from the left atrial appendage.

2. The method of claim 1, wherein the device is positioned within an inner lumen of the catheter, and releasing the device comprises applying axial force in a distal direction to the device to deploy it.

3. The method of claim 1, wherein the device is biased to a radially expanded position, and wherein the device radially expands within the left atrial appendage during the releasing step.

4. The method of claim 1, wherein the device is biased to press against an inner wall of the left atrial appendage subsequent to the releasing step.

5. The method of claim 1, wherein releasing the device from the catheter comprises detaching the device from the distal end of the catheter.

6. The method of claim 1, wherein the device comprises an expandable frame.

7. The method of claim 6, wherein the device comprises a barrier membrane attached to the expandable frame.

8. The method of claim 7, wherein the barrier membrane comprises a mesh material.

9. The method of claim 6, wherein the expandable frame comprises a plurality of strut members.

10. The method of claim 9, wherein the barrier membrane envelopes at least a proximal portion of the plurality of strut members.

11. The method of claim 9, wherein the barrier membrane comprises a proximal portion and a distal portion and wherein the distal portion is cylindrical.

12. The method of claim 6, wherein the expandable frame, when expanded, has a first portion that extends proximally and a second portion, attached to the first portion, that extends distally.

13. The method of claim 12, wherein the first portion extends radially outwardly.

14. The method of claim 13, wherein the second portion is substantially cylindrical.

15. The method of claim 12, wherein the expandable frame comprises a central hub attached to the first portion.

16. The method of claim 15, wherein the hub comprises a lumen.

* * * * *